United States Patent [19]

Dreikorn et al.

[11] Patent Number: 5,114,939
[45] Date of Patent: May 19, 1992

[54] SUBSTITUTED QUINOLINES AND CINNOLINES AS FUNGICIDES

[75] Inventors: Barry A. Dreikorn, Lawrence; Glen P. Jourdan, Morristown; Robert G. Suhr, Greenfield, all of Ind.

[73] Assignee: DowElanco, Indianapolis, Ind.

[21] Appl. No.: 324,058

[22] Filed: Mar. 16, 1989

Related U.S. Application Data

[63] Continuation-in-part of Ser. No. 150,366, Jan. 29, 1988, abandoned.

[51] Int. Cl.$^5$ ............... A01N 43/42; A01N 43/60
[52] U.S. Cl. .................. 514/248; 514/63; 514/312; 514/313; 514/314; 544/235; 546/14; 546/159; 546/162; 546/153; 546/155; 546/156
[58] Field of Search ............... 514/312, 313, 314, 248, 514/63; 546/153, 155, 156, 159, 162, 174, 176, 14; 544/235, 229

[56] References Cited

U.S. PATENT DOCUMENTS

| | | | |
|---|---|---|---|
| 2,883,382 | 4/1959 | Elslager et al. | 544/283 |
| 3,248,292 | 4/1966 | Minielli et al. | 544/283 |
| 4,444,584 | 4/1984 | Serban et al. | 546/153 |

FOREIGN PATENT DOCUMENTS

| | | | |
|---|---|---|---|
| 29319 | 5/1981 | European Pat. Off. | 544/283 |
| 0177764 | 4/1986 | European Pat. Off. | |
| 0285089 | 10/1988 | European Pat. Off. | 544/283 |
| 322133 | 6/1989 | European Pat. Off. | 544/283 |
| 326330 | 8/1989 | European Pat. Off. | 544/283 |
| 3028387 | 7/1980 | Fed. Rep. of Germany | 544/283 |
| 1233938 | 3/1971 | United Kingdom | 544/283 |
| 1364307 | 8/1974 | United Kingdom | 546/176 |
| 2052481 | 1/1981 | United Kingdom | 546/176 |
| 1598880 | 9/1981 | United Kingdom | 544/283 |
| 2135887 | 12/1984 | United Kingdom | 544/283 |

OTHER PUBLICATIONS

Grant and Hackh's Chemical Dictionary (1989, McGraw Hill, New York), p. 14.
Sugama et al., Chem. Abs., vol. 11, No. 5, entry #38746a (1989).
Hamana et al., Chem. Abs., vol. 70, No. 15, entry #68193r (1969).
Buchmann, Chem. Abs., vol. 57, entry 16760e (1960).
Hoechst AG, Derwent Abs., entry 70390E/34 Co 2 (1981).
Gildemeister et al., Liebigs Ann. Chem., vol. 9, pp. 1656-1676 (1982).
J. Chem. Soc. (B) 1967, p. 892.
J. Chem. Soc. Perkin Transactions 1, 1975, pp. 2322-2326.
Bull. de la Societe Chimique de France 1963, pp. 1161-1166.
Chemical and Pharmaceutical Bulletin 32, p. 3690 (1984).
Chemical and Pharmaceutical Bulletin 33, p. 950 (1985).
Chemie Therapeutique, vol. 2, pp. 202-212 (1967).
Chemical Abstract 86:140078g (1977).
Chemical Abstract 84:150043q (1976).
Chemical Abstract 94:156855 (1981).
Chemical Abstract 84:105533p (1976).
Chemical Abstract 68:103651w (1968).
Chemische Berichte, vol. 117, No. 4, Apr. 1984, pp. 1523-1536.
J. of Medicinal Chemistry, vol. 14, No. 4, Apr. 1971, pp. 283-286.

(List continued on next page.)

Primary Examiner—Mukund J. Shah
Assistant Examiner—E. C. Ward
Attorney, Agent, or Firm—Donald R. Stuart

[57] ABSTRACT

A fungicidal method which comprises applying to the locus of a plant pathogen a fungicidally effective but non-phytotoxic amount of a compound of the formula (1)

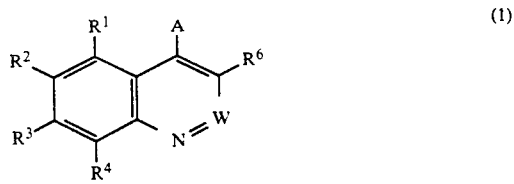

wherein:
$R^1$ to $R^4$ are independently
H, halo, ($C_1$-$C_4$) alkyl, branched ($C_3$-$C_4$) alkyl, halo ($C_1$-$C_4$) alkyl, ($C_1$-$C_4$) alkoxy, $NO_2$, or $HN_2$, at least two of $R^1$ to $R^4$ being H,
or one of $R^2$ to $R^4$ is —$NR^7$—Y—Ar or O—Y—Ar and the rest of $R^1$ to $R^4$ are H;
W is N, or $CR^5$;
$R^5$ is H, $CH_3$, Cl, O—Y—Ar, or —$NR^7$—Y—Ar;
$R^6$ is H, $CH_3$, Cl, or Br;
A is —O—Alk or —X—Y—Ar;
Alk is a $C_2$-$C_{18}$ saturated or unsaturated hydrocarbon chain, straight chain or branched, optionally substituted with halo, halo ($C_1$-$C_4$) alkoxy, ($C_3$-$C_8$) cycloalkyl, hydroxy, or acetyl;
X is O, $NR^7$, or $CR^8R^9$, provided that if one of $R^2$ to $R^5$ is $NR^7$—Y—Ar or O—Y—Ar, then X—Y—Ar is an identical group;
$R^7$ is H, ($C_1$-$C_4$) alkyl, or acetyl;
$R^8$ and $R^9$ are independently H, ($C_1$-$C_4$) alkyl, halo, or OH, or $R^8$ and $R^9$ combine to form a saturated or unsaturated carbocyclic ring comprising three to seven carbon atoms;
Y is an alkylene chain 2 to 8 carbon atoms long that optionally includes an O, S, SO, $SO_2$, or $NR^7$ group, and optionally includes a saturated or unsaturated carbocyclic ring comprising three to seven carbon atoms, and optionally is substituted with ($C_1$-$C_3$) alkyl, ($C_1$-$C_4$) alkenyl, phenyl, ($C_3$-$C_8$) cycloalkyl, hydroxy, halo, or acetyl; and
Ar is an aryl group.

28 Claims, No Drawings

OTHER PUBLICATIONS

Chimie Therapeutique, Nos. 5-6, Jul.-Oct. 1966, pp. 339-346.
Bulletin De La Societe Chimique De France, No. 1, Jan. 1971, pp. 211-214.
Bulletin De la Societe Chimiques DE France, No. 11, Nov. 1973, pp. 3175-3178.
Chemical Abstract 90:87501u (1980).
Chemical Abstract 90:198860e (1980).
Chemical Abstract 90:198861f (1980).
Chemical Abstract 90:181579x (1980).
Chemical Abstract 97:140302c (1983).

SUBSTITUTED QUINOLINES AND CINNOLINES AS FUNGICIDES

RELATED APPLICATIONS

This application is a continuation-in-part of U.S. Appln. Ser. No. 07/150,366, filed Jan. 29, 1988, now abandoned.

BACKGROUND OF THE INVENTION

1. Field of the Invention

This invention provides new compounds that have excellent plant fungicide activity. Some of the compounds have also demonstrated insecticidal and miticidal activity. The invention also provides compositions and combination products that contain a compound of the invention as active ingredient. The invention also provides fungicidal, miticidal, and insecticidal methods.

There is an acute need for new fungicides, insecticides, and miticides, because target pathogens are rapidly developing resistance to currently used pesticides. Widespread failure of N-substituted azole fungicides to control barley mildew was observed in 1983, and has been attributed to the development of resistance. At least 50 species of fungi have developed resistance to the benzimidazole fungicides. The field performance of DMI (demethylation inhibitor) fungicides, which are now widely relied on to protect cereal crops from powdery mildew, has declined since they were introduced in the 1970's. Even recent fungicides, like the acylalanines, which initially exhibited excellent control of potato late blight and grape downy mildew in the field, have become less effective because of widespread resistance. Similarly, mites and insects are developing resistance to the miticides and insecticides in current use. Resistance to insecticides in arthropods is widespread, with at least 400 species resistant to one or more insecticides. The development of resistance to some of the older insecticides, such as DDT, the carbamates, and the organophosphates, is well known. But resistance has even developed to some of the newer pyrethroid insecticides and miticides. Therefore a need exists for new fungicides, insecticides, and miticides.

SUMMARY OF THE INVENTION

This invention provides compounds of the formula (1):

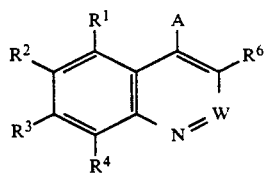

(1)

wherein:
$R^1$ to $R^4$ are independently
H, halo, ($C_1$–$C_4$) alkyl, branched ($C_3$–$C_4$) alkyl, halo ($C_1$–$C_4$) alkyl, ($C_1$–$C_4$) alkoxy, $NO_2$, or $NH_2$, at least two of $R^1$ to $R^4$ being H,
or one of $R^2$ to $R^4$ is —$NR^7$—Y—Ar or O—Y—Ar and the rest of $R^1$ to $R^4$ are H;
W is N, or $CR^5$;
$R^5$ is H, $CH_3$, Cl, O—Y—Ar, or —$NR^7$—Y—Ar;
$R^6$ is H, $CH_3$, Cl or Br;
A is —O—Alk or —X—Y—Ar;

Alk is a $C_2$–$C_{18}$ saturated or unsaturated hydrocarbon chain, straight chain or branched. Optionally substituted with halo, halo ($C_1$–$C_4$) alkoxy, ($C_3$–$C_8$) cycloalkyl, hydroxy, or acetyl;
X is O, $NR^7$, or $CR^8R^9$, provided that if one of $R^2$ to $R^5$ is $NR^7$—Y—Ar or O—Y—Ar,—then X—Y—Ar is an identiR;
$R^7$ is H, ($C_1$–$C_4$) alkyl, or acetyl;
$R^8$ and $R^9$ are independently H, ($C_1$–$C_4$) alkyl, ($C_1$–$C_4$) acyl, halo, or OH, or $R^8$ and $R^9$ combine to form a saturated or unsaturated carbocyclic ring comprising three to seven carbon atoms;
Y is an alkylene chain 2 to 8 carbon atoms long, that optionally includes an O, S, SO, $SO_2$, or $NR^7$ group, and optionally includes a saturated or unsaturated carbocyclic ring comprising three to seven carbon atoms, and optionally is substituted with ($C_1$–$C_3$) alkyl, ($C_2$–$C_4$) phenyl, ($C_3$–$C_8$) cycloalkyl, hydroxy, halo, or ($C_1$–$C_4$) acyl; and
Ar is
1,3-benzodioxolyl
fluorenyl,
pyridyl
substituted pyridyl,
indolyl,
furanyl,
substituted furanyl,
  thienyl, optionally substituted with $CH_2$ or Cl,
  thiazolyl,
  cyclopentyl,
  1-methylcyclopentyl,
  cyclohexenyl (tetrahydrophenyl),
  cyclohexyl (hexahydrophenyl),
  naphthyl,
  substituted naphthyl,
  dihydronaphthyl,
  tetrahydronaphthyl,
  decahydronaphthyl, or
  a group of the formula (2):

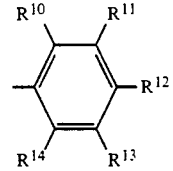

(2)

where
$R^{10}$ to $R^{14}$ are independently H, halo, I, ($C_1$–$C_{10}$) branched ($C_3$–$C_6$) alkyl, halo ($C_1$–$C_7$) alkyl, ($C_1$–$C_7$) alkoxy, halo ($C_1$–$C_7$) alkoxy, phenoxy, substituted phenoxy, phenylthio, substituted phenylthio, phenyl, substituted phenyl, $NO_2$, $NH_2$, acetoxy, OH, CN, $SiR^{15}R^{16}R^{17}$, or $OSiR^{15}R^{16}R^{17}$, where $R^{15}$, $R^{16}$, and $R^{17}$ are independently ($C_1$–$C_4$) alkyl or ($C_3$–$C_4$) branched alkyl, phenyl, or substituted phenyl, provided that unless each of $R^{10}$ to $R^{14}$ is F, $CH_3$, or H, then at least two of $R^{10}$ to $R^{14}$ are H;
or an acid addition salt of a compound of formula (1) or an N-oxide of a compound of formula (1) when W is $CR^5$
provided that the following compounds are excluded:
(1)  N-[4-(4-chlorophenyl)butyl]-7-chloro-4-quinolinamine;
(2)  N-(2-phenylethyl)-4-quinolinamine.

The final proviso excludes compounds that are known per se or that could be considered similar to known compounds.

The fungicidal combinations of the invention comprise at least 1% by weight of a compound of formula (1), or N-[4-(4-chlorophenyl)butyl]-7-chloro-4-quinolineamine or N-(2-phenylethyl)-4-quinolinamine, in combination with a second fungicidal compound.

The fungicidal compositions of the invention comprise a disease inhibiting and phytologically acceptable amount of a compound of formula (1), or N-[4-(4-chlorophenyl)butyl]-7-chloro-4-quinolinamine, or N-(2-phenylethyl)-4-quinolinamine, in combination with a phytologically-acceptable carrier.

The fungicidal method of the invention comprises applying to the locus of a plant pathogen a disease inhibiting and phytologically acceptable amount of a compound of the formula (1), or N-[4-(4-chlorophenyl)-butyl]7-chloro-4-quinolinamine, or N-(2-phenylethyl)-4-quinolinamine.

The insecticidal or miticidal combinations of the invention comprise at least 1% by weight of a compound of formula (1) in combination with a second insecticide or miticide.

The insecticide or miticide compositions of the invention comprise an insect or mite inactivating amount of a compound of formula (1) in combination with a phytologically-acceptable carrier.

The insecticide and miticide methods of the invention comprise applying to a locus of an insect or mite an insect or mite inactivating amount of a compound of formula (1), or of a combination described above.

DETAILED DESCRIPTION OF THE INVENTION

Throughout this document, all temperatures are given in degrees Celsius, and all percentages are weight percentages unless otherwise stated.

The terms "$(C_1-C_3)$ alkyl", "$(C_1-C_4)$ alkyl", and "$(C_1-C_{10})$ alkyl", when used alone, refer to straight chain alkyl radicals.

The terms "branched $(C_3-C_4)$ alkyl", and "branched $(C_3-C_6)$ alkyl" refer to all alkyl isomers containing the designated number of carbon atoms, excluding the straight chain isomers.

The terms "$(C_1-C_4)$ alkoxy" and "$(C_1-C_7)$ alkoxy" refer to straight or branched chain alkoxy groups.

The term "halo" used alone or in combination with other terms refers to F, Cl, or Br;

The term "halo $(C_1-C_7)$ alkyl" refers to a $(C_1-C_7)$ alkyl group, straight chain or branched, substituted with one or more halo groups.

The term "substituted phenyl" used alone or in combination with other terms, as in "substituted phenylthio" or "substituted phenylsulfonyl", refers to phenyl substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The term "substituted phenoxy" refers to phenoxy substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, phenyl, $NO_2$, OH, CN, $(C_1-C_4)$ alkanoyloxy, or benzyloxy.

The terms "substituted naphthyl", "substituted pyridyl" and "substituted furanyl" refer to these ring systems substituted with halo, halo $(C_1-C_4)$ alkyl, CN, $NO_2$, $(C_1-C_4)$ alkyl, $(C_3-C_4)$ branched alkyl, phenyl, $(C_1-C_4)$ alkoxy, or halo $(C_1-C_4)$ alkoxy.

The term "unsaturated hydrocarbon chain" refers to a hydrocarbon chain containing one or two sites of unsaturation.

The term "HPLC" refers to high-performance liquid chromatography.

Compounds

While all of the compounds of the invention are useful fungicides, certain classes are preferred for reasons of greater efficacy or ease of synthesis, viz:

1. compounds of formula (1) where W is $CR^5$ (i.e., substituted quinolines);
2. compounds of preferred class (1) where $R^6$ is H;
3. compounds of formula (1) where $R^6$ is H;
4. compounds of formula (1) where at least three of $R^1$ to $R^4$ are H;
5. compounds of preferred class (4) where R is F (i.e., 8-fluoroquinolines);
6. compounds of preferred class (4) where Rs is F (i.e., 7-fluoroquinolines);
7. compounds of preferred class (4) where Rs is Cl (i.e., 7-chloroquinolines);
8. compounds of preferred class (4) where Rz is F (i.e., 6-fluoroquinolines);
9. compounds of formula (1) where Y is an alkylene chain 2 to 4 carbon atoms long.
10. compounds of preferred class (9) where Y is $-(CH_2)_2-$;
11. compounds of formula (1) where Ar is
12. compounds of formula (1) where Ar is
13. compounds of formula (1) where Ar is
14. compounds of formula (1) where Ar is cyclohexenyl;
15. compounds of formula (1) where Ar is a substituted phenyl group of formula (2);
16. compounds of preferred class (15) where at least three of $R^{10}$ to $R^{14}$ are H;
17. compounds of preferred class (15) where four $R^{10}$ to $R^{14}$ are H;
18. compounds of preferred class (17) wherein one of $R^{10}$ to $R^{14}$ is Cl;
19. compounds of preferred class (18) where $R^{12}$ is Cl;
20. compounds of preferred class (17) wherein one of $R^{10}$ to $R^{14}$ is $CF_3$;
21. compounds of preferred class (17) wherein one of $R^{10}$ to $R^{14}$ is $(C_1-C_4)$ alkyl;
22. compounds of preferred class (21) wherein one of $R^{10}$ to $R^{14}$ is methyl;
23. compounds of preferred class (22) wherein $R^{12}$ is methyl;
24. compounds of preferred class (17) wherein one of $R^{10}$ to $R^{14}$ is branched $(C_3-C_6)$ alkyl;
25. compounds of preferred class (24) wherein $R^{12}$ is t-butyl;
26. compounds of preferred class (24) wherein $R^{12}$ is i-propyl;
27. compounds of preferred class (17) wherein one of $R^{10}$ to $R^{14}$ is phenyl or substituted phenyl;
28. compounds of preferred class (27) wherein $R^{12}$ is phenyl;
29. compounds of preferred class (17) wherein one of $R^{10}$ to $R^{14}$ is phenoxy or substituted phenoxy;
30. compounds of preferred class (29) wherein $R^{12}$ is phenoxy.

Compounds exhibiting particularly excellent activity against downy mildew include:
8-fluoro-N-(2-phenylethyl)-4-quinolinamine;
8-fluoro-N-[2-(4-phenyl-2-thiazolyl)ethyl]-4-quinolinamine;
8-fluoro-N-[2-[2-(trifluoromethyl)phenyl]ethyl]-4quinolinamine;
N-[2-(4-chlorophenyl)ethyl]-6-methyl-4-quinolinamine;
8-chloro-N-(2-phenylethyl)-4-quinolinamine;
8-fluoro-N-[2-(4-phenyl-2-thiazolyl)ethyl]-4-quinolinamine;
8-fluoro-N-[2-(2-naphthyl)ethyl]-4-quinolinamine;
8-fluoro-N-[2-[3-(trifluoromethyl)phenyl]ethyl]-4quinolinamine;
7-chloro-N-[2-(1-cyclohexenyl)ethyl]-4-quinolinamine;
N-[2-[4-(1-methylethyl)phenyl]ethyl]-8-fluoro-4quinolinamine;
8-fluoro-N-[2-(2-thienyl)ethyl]-4-quinolinamine;
4-[2-(3-chlorophenyl)ethoxy]-8-fluoroquinoline;
8-fluoro-4-[2-(3-(trifluoromethyl)phenyl)ethoxy]quinoline;
4-[2-(4-methylphenyl)ethoxy]quinoline;
8-fluoro-4-[2-(4-methylphenyl)ethoxy]quinoline; and
4-[2-[4-(t-butyl)phenyl]ethoxy]-8-fluoroquinoline;

Compounds exhibiting particularly excellent activity against rice blast include:
N-[2-(4-chlorophenyl)ethyl]-N-(8-fluoro-4-quinolinyl)acetamide;
N-[2-[4-(i-propyl)-phenyl]ethyl]-8-fluoro-4-quinolin
8-fluoro-N-[2-(1,1'-biphenyl)-4-yl-ethoxy]quinoline;
8-fluoro-4-[2-(3-(trifluoromethyl)phenyl)ethoxy]quinoline;
8-fluoro-4-[2-(2-naphthyl)ethoxy]quinoline;
8-fluoro-4-[2-(4-methylphenyl)ethoxy]quinoline; and
8-fluoro-4-[3-(4-(t-butyl)phenyl)propyl]quinoline;

Compounds exhibiting particularly excellent activity against a broad spectrum of plant pathogens include:
8-fluoro-N-[2-(3-phenoxyphenyl)ethyl]-4-quinolinamine;
N-[2-[4-(i-propyl)phenyl]ethyl]-8-fluoro-4-quinolin
N-[2-(1,1'-biphenyl)-3-ylethyl]-8-fluoro-4-quinolin
N-[2-(2,4-dichlorophenyl)ethyl]-8-fluoro-4-quinolin
8-fluoro-4-[3-(4-(t-butyl)phenyl)propyl]quinoline;
8-fluoro-4-[3-(4-(i-propyl)phenyl)propyl]quinoline;
8-fluoro-4-[2-(2-(trifluoromethyl)phenyl)ethoxy]quinoline;
4-[2-(4-chlorophenyl)ethoxy]-8-fluoroquinoline;
4-[2-(4-methylphenyl)ethoxy]quinoline;
8-fluoro-4-[2-(4-methylphenyl)ethoxy]quinoline;
8-fluoro-4-(2-phenylethoxy)quinoline;
8-fluoro-4-[2-(3-methylphenyl)ethoxy]quinoline;
8-fluoro-4-[2-(2-fluorophenyl)ethoxy]quinoline;
8-fluoro-4-[2-(2-methoxyphenyl)ethoxy]quinoline; and
8-fluoro-4-[2-(4-(i-propyl)phenyl)ethoxy]quinoline;

Compounds exhibiting particularly excellent activity as miticides include:
8-fluoro-N-[2-(4-iodophenyl)ethyl]-4-quinolinamine;
N-[2-(4-bromophenyl)ethyl]-8-fluoro-4-quinolinamine;
N-[2-(4-chlorophenyl)ethyl)-8-fluoro-4-quinolinamine;
N-[2-(4-chlorophenyl)ethyl]-N-ethyl-8-fluoro-4-quinolinamine;
N-3-(1,1'-biphenyl)-4-ylpropyl]-8-fluoro-4-quinolin
8-fluoro-N-[2-(4-phenoxyphenyl)ethyl]-4-quinolinamine;
N-2-4-(t-butyl)phenyl]ethyl]-8-fluoro-4-quinolin
N-[2-[4-(i-propyl)phenyl]ethyl]-8-fluoro-4-quinolin
N-2-(4-chlorophenyl)ethyl]-6-fluoro-4-quinolinamine;
8-fluoro-N-[2-(1,1'-biphenyl)-4-yl-ethoxy]quinoline;
4-[2-(3-chlorophenyl)ethoxy]-8-fluoroquinoline;
4-2-[4-(t-butyl)phenyl]ethoxy]-8-fluoroquinoline;
8-fluoro-4-[2-(4-(i-propyl)phenyl)ethoxy]quino
8-fluoro-4-2-(3-(trifluoromethyl)phenyl)ethoxy]quinoline;
8-fluoro-4-2-(4-methoxyphenyl)ethoxy]quinoline;
8-fluoro-4-2-(3-phenoxyphenyl)ethoxy]quinoline;
8-fluoro-4-2-(2-naphthyl)ethoxy]quinoline;
7-fluoro-4-2-(1,1'-biphenyl)-2-yl-ethoxy]quinoline;
7-chloro-4-[2-(1,1'-biphenyl)-4-yl-ethoxy]quinoline;
4-chloro-4-[2-(4-(t-butyl)phenyl)ethoxy]quinoline;
4-[2-(4-(t-butyl)phenyl)ethoxy]-7-fluoroquinoline;
8-2-(1,1'-biphenyl)-4-ylethoxy]-7-fluoroquinoline;
8-fluoro-4-(3-phenylpropyl)quinoline;
8-fluoro-4-[3-(4-methylphenyl)propyl]quinoline; and
8-fluoro-4-[3-[3-(trifluoromethyl)phenyl]propyl]quinoline.

Synthesis

The compounds of this invention are made using well known chemical procedures. The required starting materials are commercially available, or they are readily synthesized using standard procedures.

Synthesis of Compounds Wherein A is O—Y—Ar or —O—Alk

The compounds of formula (1) wherein A is O—Y—Ar or O—Alk were made by condensing a compound of formula (3):

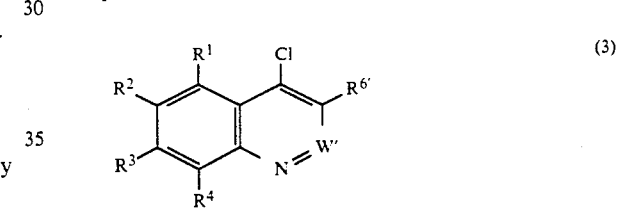

where $R^1$ to $R^4$ are as previously defined, $R^{6'}$ is H or $CH_3$, and W' is N or $CR^{5'}$, where $R^{5'}$ is H, Cl, or $CH_3$, with an alcohol of the formula (4a or 4b):

HO—Y—Ar     (4a)

HO—Alk     (4b)

where
Y, Ar, and Alk are as previously defined.

The reaction is preferably carried out in the presence of a strong base, such as sodium hydride, in an inert organic solvent, such as DMF, at a temperature in the range of 0° to 25° C.

Synthesis of Compounds Wherein A is $NR^7$—Y—Ar

The compounds of formula (1) wherein A is $NR^7$—Y—Ar were prepared by condensing a compound of formula (3) with an amine of the formula (5)

where
$R^7$ is H or ($C_1$–$C_4$) alkyl, and Y and
Ar are as previously defined.
The chloride of formula (3) is allowed to react with an appropriate amine, preferably at elevated temperature (100°–180° C.), and preferably in the presence of an acid accepter, such as triethylamine. The reaction may be carried out neat, or in an inert organic solvent.

Compounds where $R^7$ is acetyl were prepared by reacting amines of formula (1) where $R^7$ is H, with an acylating agent, such as an acetyl chloride or acetic anhydride. In cases where the starting material of formula (3) is one wherein W' is CCl, a mixture of products is obtained, which are separable using HPLC.

Synthesis of Compounds Wherein A is $CR^8R^9$—Y—Ar

The compounds of formula (1) wherein A is $CR^8R^9$—Y—Ar can be made using the process described in *J. Heterocyclic Chemistry*, Vol. 14, p. 1081-1083 (1977) by A. Scoville and F. X. Smith. This process entails preparation of a 5-substituted-5-(4-quinolyl)barbituric acid of the formula (6)

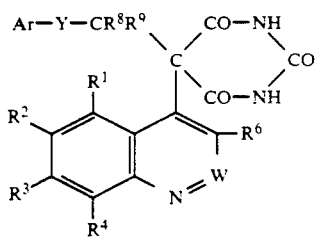

(6)

which is then hydrolyzed and decarboxylated by dissolving the intermediate in a solution of sodium hydroxide and water, refluxing, then making the solution slightly acidic with hydrochloric acid and again refluxing.

Derivatives

The compounds of formula (1) wherein $R^6$ is Cl are prepared by halogenating a compound of formula (1) wherein $R^6$ is H with $POCl_3/PCl_5$.

The compounds of formula (1) wherein Rs is Br are prepared by reacting a compound of formula (1) wherein $R^6$ is H with $Br_2$ in acetic acid.

N-oxides of the compounds of formula (1) are prepared by reacting the compound of formula (1) with an oxidizing agent, such as 3-chloroperoxybenzoic acid or hydrogen peroxide, in a non-reactive organic solvent, such as methylene chloride or chloroform, at $-20°$ C. to room temperature, preferably at about $0°$ C.

The acid addition salts of compounds of formula (1) are obtained in the usual way.

Accordingly, the invention also provides a process for preparing a compound of formula (1) which comprises:

(a) condensing a compound of formula (3):

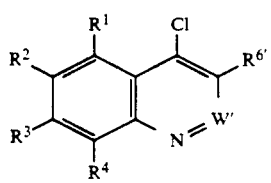

(3)

where $R^1$ to $R^4$ are as previously defined. $R^{6'}$ is H or $CH_3$, and W' is N or $CR^{5'}$, where $R^{5'}$ is H, Cl, or $CH_3$, with an alcohol of the formula (4a or 4b):

HO—Y—Ar, (4a)

HO—Alk (4b)

where

Y, Ar, and Alk are as previously defined to provide a compound of formula (1) wherein A is O—Y—Ar or O—Alk; or (b) condensing a compound of formula (3) with an amine of the formula (5)

(5)

where $R^7$ is H or ($C_1$-$C_4$) alkyl, and Y and

Ar are as previously defined to provide a compound of formula (1) wherein A is $-NR^7$—Y—Ar; or (c) reacting an amine of formula (1) where $R^7$ is H, with acetyl chloride or acetic anhydride to provide a compound of formula (1) wherein A is $-NR^7$—Y—Ar where $R^7$ is acetyl; or (d) hydrolyzing and decarboxylating a compound of the formula (6)

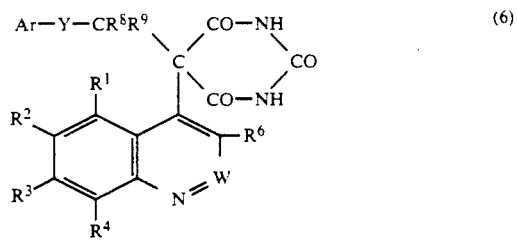

(6)

to provide a compound of formula (1) wherein A is $-CR^8R^9$—Y—Ar or (e) halogenating a compound of formula (1) wherein $R^6$ is H with $POCl_3/PCl_5$ to provide a compound of formula (1) wherein $R^6$ is Cl; or (f) reacting a compound of formula (1) where $R^6$ is H with $Br_2$ in acetic acid to provide a compound of formula (1) where $R^6$ is Br; or (g) oxidizing a compound of formula (1) wherein W is CRs to provide the corresponding N-oxide.

Preparation of Quinoline Starting Materials

Quinoline starting materials can be synthesized using a variety of known procedures.

*Organic Syntheses*, collective volume 3, 1955, pp. 272-75, gives a procedure for preparing 4,7-dichloroquinoline, and other polysubstituted quinolines. Another general procedure is described in *Tetrahedron*, vol. 41, pp. 3033-36 (1985).

Many of the quinoline starting materials used in the following examples were prepared by the protocol shown in the following reaction scheme

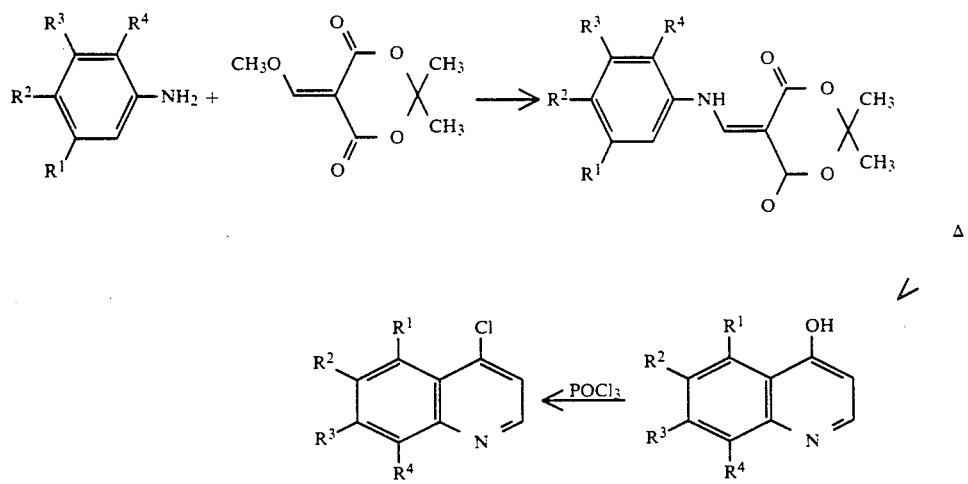

In cases where mixtures of isomeric products were obtained, the mixture of substituted 4-quinolones was chlorinated under standard conditions, and the 4-chloroquinolines were separated by liquid chromatography.

Preparation of Cinnoline Starting Materials

Cinnoline analogs are prepared via published methods. (C. M. Atkinson and J. C. Simpson - *J. Chem. Soc. London*, 1947, 232). The substituted 2-amino-acetophenone is diazotized at 0°–5° C. in water using sodium nitrite and mineral acid, and the intermediate diazonium salt is trapped by the enolic component of the ketone to provide the requisite 4-hydroxycinnoline. Routine chlorination provides the desired intermediates.

EXAMPLES 1 TO 328

Tables 1–12 identify compounds actually prepared by the above described general procedures, and give each compound's melting point. Specific illustrative preparations of the compounds of Examples 4, 10, 25, 69, 97, 154, 159, 173, 181, 186, 209, 212, 221, 238, 251, and 261 follow the table.

TABLE 1

N-(2-phenylethyl)-4-quinolinamines

| EXAMPLE NUMBER | COMPOUND | M.P. |
|---|---|---|
| 1 | 6-methoxy-N-(2-phenylethyl)-4-quinolineamine | NA |
| 2* | N-(2-phenylethyl)-4-quinolinamine | 159–160° C. |
| 3 | 6-ethyl-N-(2-phenylethyl)-4-quinolinamine | 119–120° C. |
| 4 | N-ethyl-N-(2-phenylethyl)-4-quinolinamine | oil |
| 5 | 8-fluoro-N-(2-phenylethyl)-4-quinolinamine | 149–150° C. |
| 6 | 2-methyl-N-(2-phenylethyl)-4-quinolinamine | 153–154° C. |
| 7 | 6,8-difluoro-N-(2-phenylethyl)-4-quinolinamine | 196–197° C. |
| 8 | 7-fluoro-N-(2-phenylethyl)-4-quinolinamine | 160–161° C. |
| 9 | 6-fluoro-N-(2-phenylethyl)-4-quinolinamine | 163–164° C. |
| 10 | N-[2-(4-chlorophenyl)ethyl]-N-(8-fluoro-4-quinolinyl)-acetamide | oil |
| 11 | 8-fluoro-N-[2-(4-iodo-phenyl)ethyl]-4-quinolinamine | 221–223° C. |

TABLE 1-continued

N-(2-phenylethyl)-4-quinolinamines

| EXAMPLE NUMBER | COMPOUND | M.P. |
|---|---|---|
| 12 | N-[2-(4-bromophenyl)ethyl]-6,8-difluoro-4-quinolinamine | 235–238° C. |
| 13 | N-[2-(4-bromophenyl)ethyl]-8-(trifluoromethyl)-4-quinolinamine | 188–190° C. |
| 14 | N-[2-(4-chlorophenyl)ethyl]-6-methyl-4-quinolinamine | 123–125° C. |
| 15 | N-[2-(4-chlorophenyl)ethyl]-6,8-dimethyl-4-quinolinamine | 113–115° C. |
| 16 | N-[2-(4-chlorophenyl)ethyl]-6-methoxy-4-quinolinamine | 155–157° C. |
| 17 | N-(2-phenylethyl)-7-(trifluoromethyl)-4-quinolinamine | 138–139° C. |
| 18 | N-[2-(4-bromophenyl)ethyl]-4-quinolinamine | 176–177° C. |
| 19 | N-[2-(4-methylphenyl)ethyl]-4-quinolinamine | 159–160° C. |
| 20* | N-[2-(4-chlorophenyl)ethyl]-4-quinolinamine | 162–163° C. |
| 21 | N-(2-phenylpropyl)-4-quinolinamine | 126–127° C. |
| 22 | N-[2-(4-methoxyphenyl)-ethyl]-4-quinolinamine | 127–128° C. |
| 23 | N-(2,2-diphenylethyl)-4-quinolinamine | 154–155° C. |
| 24 | N-(1-methyl-2-phenylethyl)-4-quinolinamine | 132–133° C. |
| 25 | 2-chloro-N-(2-phenylethyl)-4-quinolinamine | 132–133° C. |
| 26 | α-[(4-quinolinylamino)-methyl]benzenemethanol | 195–197° C. |
| 27 | 8-methyl-N-(2-phenylethyl)-4-quinolinamine | 127–128° C. |
| 28 | 6,8-dimethyl-N-(2-phenylethyl)-4-quinolinamine | 114–115° C. |
| 29 | 8-ethyl-N-(2-phenyl)-4-quinolinamine | 98–99° C. |
| 30 | 6-methyl-N-(2-phenylethyl)-4-quinolinamine | 124–125° C. |
| 31 | 7-chloro-N-(2-phenylethyl)-4-quinolinamine | 137–138° C. |
| 32 | 7,8-dimethyl-N-(2-phenylethyl)-4-quinolinamine | 183–185° C. |
| 33 | 8-chloro-N-(2-phenylethyl)-4-quinolinamine | 156–157° C. |
| 34 | N-(2,2-diphenylpropyl)-4-quinolinamine | 110–111° C. |
| 35 | N-[2-(4-fluorophenyl)ethyl]-4-quinolinamine | 121–122° C. |
| 36 | 8-fluoro-N-[2-(4-methoxyphenyl)ethyl]-4-quinolinamine | 165–167° C. |
| 37 | 7-chloro-N-[2-(4-chlorophenyl)ethyl]-4-quinolinamine | 190–192° C. |

TABLE 1-continued

N-(2-phenylethyl)-4-quinolinamines

| EXAMPLE NUMBER | COMPOUND | M.P. |
|---|---|---|
| 38 | N-[2-(3,4-dimethoxyphenyl)ethyl]-8-fluoro-4-quinolinamine | 127–130° C. |
| 39 | 8-fluoro-N-[2-(3-phenoxyphenyl)ethyl]-4-quinolinamine | 83–85° C. |
| 40 | 6,8-difluoro-N-(2-[1,1'-biphenyl]-4-ylethyl)-4-quinolinamine | 216–218° C. |
| 41 | N-[2-(4-chlorophenyl)ethyl]-6,8-difluoro-4-quinolinamine | 218–220° C. |
| 42 | N-[2-(4-methoxyphenyl)ethyl]-7-(trifluoromethyl)-4-quinolinamine | 107–109° C. |
| 43 | 7-chloro-N-[2-(3-methoxyphenyl)ethyl]-4-quinolinamine | 155–158° C. |
| 44 | 7-chloro-N-[2-(2,4-dichlorophenyl)ethyl]-4-quinolinamine | 168–170° C. |
| 45 | 7-chloro-N-[2-(3,5-dimethoxyphenyl)ethyl]-4-quinolinamine | 117–120° C. |
| 46 | N-[2-(4-methoxyphenyl)ethyl]-6-methyl-4-quinolinamine | 120–123° C. |
| 47 | N-[2-(4-chlorophenyl)ethyl]-7-(trifluoromethyl)-4-quinolinamine | 153–155° C. |
| 48 | N-[2-(3,4-dimethoxyphenyl)ethyl]-7-(trifluoromethyl)-4-quinolinamine | oil |
| 49 | N-[2-(3-chlorophenoxy)ethyl]-8-fluoro-4-quinolinamine | 161–163° C. |
| 50 | 7-chloro-N-[2-(4-methylphenyl)ethyl]-4-quinolinamine | 155–158° C. |
| 51 | 8-chloro-N-[2-(4-fluorophenyl)ethyl]-4-quinolinamine | 194–196° C. |
| 52 | N-[2-(2,4-dichlorophenyl)ethyl]-8-(trifluoromethyl)-4-quinolinamine | 158–160° C. |
| 53 | N-[2-(2,4-dichlorophenyl)ethyl]-6-methyl-4-quinolinamine | 180–182° C. |
| 54 | 7-chloro-6-methoxy-2-methyl-N-(2-phenylethyl)-4-quinolinamine | 180–181° C. |
| 55 | N-[2-(2-methoxyphenyl)ethyl]-4-quinolinamine | 127–128° C. |
| 56 | N-[2-(4-chlorophenyl)ethyl]-6-fluoro-4-quinolinamine | 134–138° C. |
| 57 | N-[2-(4-chlorophenyl)ethyl]-2-methyl-6-fluoro-4-quinolinamine | 104–106° C. |
| 58 | 6-methyl-N-[2-(4-methylphenyl)ethyl]-4-quinolinamine | 122–124° C. |
| 59 | 5,7-dichloro-N-[2-(4-chlorophenyl)ethyl]-4-quinolinamine | 113–115° C. |
| 60 | 7-chloro-N-[2-(3-phenoxyphenyl)ethyl]-4-quinolinamine | 128–130° C. |
| 61 | 8-methyl-N-[2-(4-chlorophenyl)ethyl]-4-quinolinamine | 118–120° C. |
| 62 | 8-fluoro-N-(2-cyclohexyl-2-phenylethyl)-4-quinolinamine | 74–75° C. |
| 63 | 8-fluoro-N-[2-(2-phenoxyphenyl)ethyl]-4-quinolinamine | 131–133° C. |
| 64 | 7,8-dimethyl-N-[2-(2-phenoxyphenyl)ethyl]-4-quinolinamine | 124–126° C. |
| 65 | N-[2-(2,6-difluorophenyl)ethyl]-8-fluoro-4-quinolinamine | 203–204° C. |
| 66 | 8-fluoro-N-[2-(3-fluorophenyl)ethyl]-4-quinolinamine | 174–175° C. |
| 67 | N-[2-(3,5-dimethoxyphenyl)ethyl]-4-quinolinamine | 122–123° C. |
| 68 | 8-fluoro-N-[2-(2-methoxyphenyl)ethyl]-4-quinolinamine | 163–164° C. |
| 69 | 3-chloro-N-(2-chloro-2-phenylethyl)-4-quinolinamine | oil |
| 70 | N-(2-phenylethyl)-5,7-bis-(trifluoromethyl)-4-quinolinamine | oil |
| 71 | 8-fluoro-N-[2-(4-methylphenyl)ethyl]-4-quinolinamine | 176–177° C. |
| 72 | N-[2-(1,1'-biphenyl)-3-ylethyl]-8-fluoro-4-quinolinamine | 140–142° C. |
| 73 | 8-fluoro-4-[(2-phenylethyl)amino]-3-quinolinemethanol | 107–108° C. |
| 74 | N-[2-(3-chlorophenyl)ethyl]-8-fluoro-4-quinolinamine | 191–192° C. |
| 75 | N-[2-(3,4-dichlorophenyl)ethyl]-8-fluoro-4-quinolinamine | 204–206° C. |
| 76 | N-[2-(2,4-dichlorophenyl)ethyl]-8-fluoro-4-quinolinamine | 187–189° C. |
| 77 | 8-fluoro-N-(2-phenylpropyl)-4-quinolinamine | 136–137° C. |
| 78 | 8-fluoro-N-[2-(4-fluorophenyl)ethyl]-4-quinolinamine | 171–173° C. |
| 79 | N-[2-(4-chlorophenyl)propyl]-8-fluoro-4-quinolinamine | 126–127° C. |
| 80 | N-(2,2-diphenylpropyl)-8-fluoro-4-quinolinamine | 56–58° C. |
| 81 | 8-fluoro-N-(2-phenylbutyl)-4-quinolinamine | 114–116° C. |
| 82 | N-[2-(2-chlorophenyl)ethyl]-8-fluoro-4-quinolinamine | 175–177° C. |
| 83 | 8-fluoro-N-[2-[4-(trifluoromethyl)phenyl]ethyl]-4-quinolinamine | 205–206° C. |
| 84 | 7-chloro-N-[2-(4-methoxyphenyl)ethyl]-4-quinolinamine | 122–124° C. |
| 85 | 8-chloro-N-[2-(4-chlorophenyl)ethyl]-4-quinolinamine | 185–187° C. |
| 86 | N-[2-(4-chlorophenyl)ethyl]-8-(trifluoromethyl)-4-quinolinamine | 192–194° C. |
| 87 | 8-chloro-N-[2-(4-methylphenyl)ethyl]-4-quinolinamine | 184–186° C. |
| 88 | N-[2-(4-chlorophenyl)ethyl]-7,8-dimethyl-4-quinolinamine | 177–179° C. |
| 89 | 8-fluoro-N-[2-(4-methylphenyl)ethyl]-4-quinolinamine | 153–154° C. |
| 90 | 8-fluoro-N-[2-(4-phenoxyphenyl)ethyl]-4-quinolinamine | 109–111° C. |
| 91 | 3-bromo-8-fluoro-N-(2-phenylethyl)-4-quinolinamine | 95–97° C. |
| 92 | 8-fluoro-N-(1-methyl-2-phenylethyl)-4-quinolinamine | 166–168° C. |
| 93 | 2,8-dichloro-N-(2-phenylethyl)-4-quinolinamine | 190–192° C. |
| 94 | N-[2-(4-bromophenyl)ethyl]-8-fluoro-4-quinolinamine | 198–199° C. |
| 95 | 8-fluoro-N-[2-[3-(trifluoromethyl)phenyl]ethyl]-4-quinolinamine | 161–162° C. |
| 96 | N-[2-(4-chlorophenyl)ethyl]-8-fluoro-4-quinolinamine | 176–177° C. |
| 97 | 8-fluoro-N-[2-(2-(trifluoromethyl)phenyl]ethyl]-4-quinolinamine | 157–158° C. |
| 98 | 2-chloro-N-[2-(2,4-dichlorophenyl)ethyl]-8-fluoro-4-quinolinamine | 199–200° C. |
| 99 | N-(2-phenylethyl)-8-(trifluoromethyl)-4-quinolinamine | 151–152° C. |
| 100 | 7-chloro-N-[2-(2-methoxyphenyl)ethyl]-4-quinolinamine | 140–142° |
| 101 | 7-chloro-N-[2-(3,4-dichlorophenyl)ethyl]-4-quinolinamine | 128–130° C. |
| 102 | N-[2-(4-chlorophenyl)ethyl]-2-methyl-4-quinolinamine | 176–178° C. |
| 103 | N-[2-(2-chloro-6-fluorophenyl)ethyl]-8-fluoro-4- | 198–201° C. |

TABLE 1-continued

N-(2-phenylethyl)-4-quinolinamines

| EXAMPLE NUMBER | COMPOUND | M.P. |
|---|---|---|
| 104 | N-[2-(2,4-dichlorophenyl)-ethyl]-7-(trifluoromethyl)-4-quinolinamine | 175–177° C. |
| 105 | N-[2-(4-chlorophenyl)ethyl]-N-ethyl-8-fluoro-4-quinolinamine | oil |
| 106 | 7-chloro-N-(4-fluorophenyl)-N-methyl-4-quinolinamine | 83–85° C. |
| 107 | 7-chloro-N-[2-[3-(trifluoromethyl)phenyl]ethyl]-4-quinolinamine | 184–186° C. |
| 108 | N-[2-(3-bromophenyl)ethyl]-8-fluoro-4-quinolinamine | 206–208° C. |
| 109 | N-[2-(4-chlorophenyl)ethyl]-5,8-dimethyl-4-quinolinamine | oil |
| 110 | N(4)-[2-(4-chlorophenyl)ethyl]-4,8-quinolinamine | oil |
| 111 | N-[2-[4-(t-butyl)phenyl]ethyl]-8-fluoro-4-quinolinamine | 198–200° C. |
| 112 | N-[2-(2,3,4,5,6-tetramethylphenyl)ethyl]-8-fluoro-4-quinolinamine | 204–207° C. |
| 113 | N-[2-(1,1-biphenyl)-4-yl-ethyl]-8-fluoro-4-quinolinamine | 178–180° C. |
| 114 | N-[2-[4-(i-propyl)phenyl]ethyl]-8-fluoro-4-quinolinamine | 157–159° C. |
| 115 | N-[2-(2-chlorophenyl)ethyl]-8-chloro-4-quinolinamine | 205–207° C. |
| 116 | 2-chloro-8-fluoro-N-(2-phenylethyl)-4-quinolinamine | 158–159° C. |
| 117 | 8-fluoro-N-[2-(4-nitrophenyl)ethyl]-4-quinolinamine | 234–236° C. |
| 118 | N-[2-(2,6-dichlorophenyl)-ethyl]-8-fluoro-4-quinolinamine | 222–224° C. |
| 119 | N-[2-(3,5-dimethoxyphenyl)-ethyl]-8-fluoro-4-quinolinamine | 131–132° C. |
| 120 | N-(2-phenylcyclopropyl)-4-quinolinamine | 147–148° C. |
| 121 | N-[2-(4-chlorophenyl)ethyl]-N-(6-fluoro-4-quinolinyl)acetamide | 87–88° C. |
| 122 | N-[2-(4-methylphenyl)ethyl]-N-(6-methyl-4-quinolinyl)acetamide | 97–98° C. |
| 123 | 8-fluoro-N-(2-phenylcyclopropyl)-4-quinolinamine | 204–205° C. |
| 124 | N-[2-(4-chlorophenyl)ethyl]-N-(7-chloro-4-quinolinyl)acetamide | oil |
| 125 | N-(7-chloro-4-quinolinyl)-N-[2-(4-methoxyphenyl)ethyl]acetamide | oil |
| 126 | N-(7-chloro-4-quinolinyl)-N-[2-[3-(trifluoromethyl)phenyl]ethyl]acetamide | oil |
| 127 | N-[2-(2,4-dichlorophenyl)ethyl]-N-[7-(trifluoromethyl)-4-quinolinyl]acetamide | oil |
| 128 | N-[4-(t-butyl)phenyl]ethyl-N-(8-fluoro-4-quinolinyl)acetamide | 126–128° C. |
| 129 | N-[2-[4-(i-propyl)phenyl]ethyl]-N-(8-fluoro-4-quinolinyl)acetamide | 82–84° C. |
| 130 | N-[2-(1,1'-biphenyl)-4-ylethyl]-N-(8-fluoro-4-quinolinyl)acetamide | oil |
| 131 | N-[2-(pentamethylphenyl)ethyl]-N-(8-fluoro-4-quinolinyl)acetamide | oil |
| 132 | N-[2-(2-chlorophenyl)ethyl]-N-(8-chloro-4-quinolinyl)acetamide | 104–106° C. |
| 133 | N-[2-(4-methoxyphenyl)ethyl]-7,8-dimethyl-4-quinolinamine | 183–185° C. |

*not a compound claimed per se, but one used in the claimed compositions and methods.

TABLE 2

N-(3-phenylpropyl)-4-quinolinamines

| EXAMPLE NUMBER | COMPOUND | M.P. |
|---|---|---|
| 134 | 7-chloro-N-[3-(1,1'-biphenyl)-4-ylpropyl]-4-quinolinamine | 122–124° C. |
| 135 | N-[3-(4-chlorophenyl)propyl]-8-fluoro-4-quinolinamine | 134–136° C. |
| 136 | N-[3-(4-chlorophenyl)propyl]-7-chloro-4-quinolinamine | 177–179° C. |
| 137 | N-[3-(1,1'-biphenyl)-4-ylpropyl]-8-fluoro-4-quinolinamine | 124–127° C. |
| 138 | 8-fluoro-N-(1-methyl-3-phenylpropyl)-4-quinolinamine | 164–166° C. |
| 139 | N-(3-phenylpropyl)-4-quinolinamine | 96–97° C. |

TABLE 3

N-(4-phenylbutyl)-4-quinolinamines

| EXAMPLE NUMBER | COMPOUND | M.P. |
|---|---|---|
| 140 | 8-fluoro-N-[4-(4-chlorophenyl)butyl]-4-quinolinamine | 110–112° C. |
| 141 | N-[4-(4-chlorophenyl)butyl]-N-(8-fluoro-4-quinolinyl)acetamide | oil |

TABLE 4

N-Arylalkyl-4-quinolinamines

| EXAMPLE NUMBER | COMPOUND | M.P. |
|---|---|---|
| 142 | N-[2-(1-cyclohexenyl)ethyl]-5,8-dimethyl-4-quinolinamine | 78–81° C. |
| 143 | N-[2-(1-cyclohexenyl)ethyl]-8-fluoro-4-quinolinamine | 153–155° C. |
| 144 | N-[2-(1-cyclohexenyl)ethyl]-6,8-dimethyl-4-quinolinamine | 114–116° C. |
| 145 | N-[2-(1-cyclohexenyl)ethyl]-6-ethyl-4-quinolinamine | 135–137° C. |
| 146 | N-[2-(1-cyclohexenyl)ethyl]-N-(6-fluoro-4-quinolinyl)acetamide | 66–68° C. |
| 147 | N-[2-(2-thienyl)ethyl]-4-quinolinamine | 153–154° C. |
| 148 | N-[2-(3-thienyl)ethyl]-4-quinolinamine | 156–157° C. |
| 149 | 6,8-difluoro-N-[2-(2-thienyl)ethyl]-4-quinolinamine | 175–176° C. |
| 150 | 6,8-difluoro-N-[2-(3-thienyl)ethyl]-4-quinolinamine | 191–192° C. |
| 151 | N-[2-(1-naphthyl)ethyl]-4-quinolinamine | 149–150° C. |
| 152 | N-[2-(2-naphthyl)ethyl]-4-quinolinamine | 160–161° C. |
| 153 | N-[2-(2-thienyl)ethyl]-7-(trifluoromethyl)-4-quinolinamine | 131–132° C. |
| 154 | 8-fluoro-N-[2-(4-phenyl-2-thiazolyl)ethyl]-4-quinolinamine | 134–135° C. |
| 155 | 8-chloro-N-[2-(1-naphthyl)ethyl]-4-quinolinamine | 205–206° C. |
| 156 | 8-chloro-N-[2-(2-naphthyl)ethyl]-4-quinolinamine | 206–208° C. |
| 157 | α-[[(8-fluoro-4-quinolinyl)amino]methyl]-2-naphthalenemethanol | 182–185° C. |
| 158 | 8-fluoro-N-[2-(1-naphthyl)ethyl]-4-quinolinamine | 152–153° C. |
| 159 | 8-fluoro-N-[2-(2-naphthyl)ethyl]-4-quinolinamine | 173–174° C. |
| 160 | N-[2-(1-cyclohexenyl)ethyl]-N-(5,8-dimethyl-4-quinolinyl)acetamide | oil |
| 161 | N-(2-cyclohexylethyl)-N-(8-fluoro-4-quinolinyl)acetamide | oil |
| 162 | 8-fluoro-N-[2-(5-methyl-2-thienyl)ethyl]-4-quinolinamine | 161–163° C. |
| 163 | N-[2-(5-chloro-2-thienyl)ethyl]-8-fluoro-4-quinolinamine | 167–168° C. |
| 164 | 8-fluoro-N-[2-(1H-imidazol-4-yl)ethyl]-4-quinolinamine | 230° C. |
| 165 | 7-chloro-N-[2-(1-cyclohexenyl)ethyl]-4-quinolinamine | 161–163° C. |

TABLE 4-continued
N-Arylalkyl-4-quinolinamines

| EXAMPLE NUMBER | COMPOUND | M.P. |
|---|---|---|
| 166 | 7-chloro-N-[2-(2-naphthyl)-ethyl]-4-quinolinamine | 156–158° C. |
| 167 | N-[2-(1-cyclohexenyl)ethyl]-7-(trifluoromethyl)-4-quinolinamine | 158–160° C. |
| 168 | N-[2-(1-cyclohexenyl)ethyl]-6-fluoro-4-quinolinamine | 129–131° C. |
| 169 | N-[2-(2-naphthyl)ethyl]-7-(trifluoromethyl)-4-quinolinamine | 127–130° C. |
| 170 | 8-fluoro-N-[1-methyl-2-(2-thienyl)ethyl]-4-quinolinamine | 217–219° C. |
| 171 | N-[1-methyl-2-(2-thienyl)ethyl]-4-quinolinamine | 167–168° C. |
| 172 | 8-chloro-N-[2-(2-thienyl)ethyl]-4-quinolinamine | 161–162° C. |
| 173 | 8-fluoro-N-[2-(2-thienyl)ethyl]-4-quinolinamine | 157–158° C. |
| 174 | N-[2-(2,3-dihydro-1,4-benzodioxin-2-yl)ethyl]-8-fluoro-4-quinolinamine | 170–171° C. |
| 175 | 8-fluoro-N-[2-(3-thienyl)ethyl]-4-quinolanamine | 163–164° C. |
| 176 | 8-fluoro-N-[2-(1H-indol-3-yl)ethyl]-4-quinolinamine | 205–206° C. |
| 177 | N-(2-cyclohexylethyl)-8-fluoro-4-quinolinamine | 145–147° C. |
| 178 | N-(2-cyclohexylethyl)-6,8-dimethyl-4-quinolinamine | 155–157° C. |
| 179 | N-[2-(1-cyclohexenyl)ethyl]-N-(6,8-dimethyl-4-quinolinyl)acetamide | oil |
| 180 | 8-fluoro-N-[2-(2-pyridinyl)ethyl]-4-quinolinamine | 143–144° C. |

TABLE 5
Bis[2-phenylethyl]quinolinediamines

| EXAMPLE NUMBER | COMPOUND | M.P. |
|---|---|---|
| 181 | N,N'-bis(2-phenylethyl)-2,4-quinolinediamine | 70–71° C. |
| 182 | N,N'-(2,4-quinolinediyl)bis[N-[2-(4-chlorophenyl)ethyl]acetamide] | oil |
| 183 | 8-fluoro-N,N'-bis(2-phenylethyl)-2,4-quinolinediamine | oil |
| 184 | N,N'-bis(2-phenylpropyl)-2,4-quinolinediamine | oil |
| 185 | N,N'-bis[2-(4-chlorophenyl)ethyl]-4,6-quinolinediamine | 135–137° C. |
| 186 | N,N'-bis[2-(4-chlorophenyl)ethyl]-4,7-quinolinediamine | 55–60° C. |
| 187 | N,N'-bis[2-(4-methoxyphenyl)ethyl]-4,7-quinolinediamine | 140–150° C. |
| 188 | N,N'-bis[2-(4-chlorophenyl)ethyl]-8-fluoro-2,4-quinolinediamine | oil |
| 189 | N,N'-bis(2-phenylethyl)-4,8-quinolinediamine | 83–84° C. |
| 190 | N,N'-bis[2-(2,4-dichlorophenyl)ethyl]-8-fluoro-2,4-quinolinediamine | 116–117° C. |
| 191 | N,N'-(4,7-quinolinediyl)bis[N-[2-(4-chlorophenyl)ethyl]acetamide] | oil |

TABLE 6
Bis[2-arylethyl]quinolinediamines

| EXAMPLE NUMBER | COMPOUND | M.P. |
|---|---|---|
| 192 | N,N'-bis[2-(1-cyclohexen-yl)ethyl]-4,6-quinolinediamine | 129–131° C. |

TABLE 7
4-(2-phenylethoxy)quinolines

| EXAMPLE NUMBER | COMPOUND | M.P. |
|---|---|---|
| 193 | 2-chloro-8-fluoro-4-[2-(4-methylphenyl)ethoxy]quinoline | 76–77° C. |
| 194 | 5,7-dichloro-4-[2-(1,1'-biphenyl)-4-ylethoxy]quinoline | 100–102° C. |
| 195 | 4-[2-(3-methoxyphenyl)ethoxy]-8-fluoroquinoline | 90–91° C. |
| 196 | 8-fluoro-4-[2-(4-methoxyphenyl)ethoxy]quinoline | 70–71° C. |
| 197 | 8-fluoro-4-[2-(3-phenoxyphenyl)ethoxy]quinoline | 73–75° C. |
| 198 | 8-bromo-4-[2-(4-(t-butyl)phenyl)ethoxy]quinoline | 115–118° C. |
| 199 | 4-[2-(3,4-dimethoxyphenyl)ethoxy]-8-fluoroquinoline | 113–114° C. |
| 200 | 8-fluoro-N-[2-(1,1'-biphenyl)-4-yl-ethoxy]quinoline | 141–142° C. |
| 201 | 4-[2-(3-chlorophenyl)ethoxy]-8-fluoroquinoline | 76–77° C. |
| 202 | 7-chloro-4-(2-phenylethoxy)quinoline | oil |
| 203 | 8-fluoro-4-[2-(3-(trifluoromethyl)phenyl)ethoxy]quinoline | 98–99° C. |
| 204 | 7-chloro-4-[2-(4-methylphenyl)ethoxy]quinoline | 87–88° C. |
| 205 | 8-fluoro-4-[2-(2-methylphenyl)ethoxy]quinoline | 72° C. |
| 206 | 8-fluoro-4-[2-(2-(trifluoromethyl)phenyl)ethoxy]quinoline | 60° C. |
| 207 | 8-chloro-4-(2-phenylethoxy)quinoline | 73–74° C. |
| 208 | 4-(2-phenylethoxy)quinoline | oil |
| 209 | 4-[2-(4-chlorophenyl)ethoxy]-8-fluoroquinoline | 138–140° C. |
| 210 | 4-[2-(4-methylphenyl)ethoxy]quinoline | 59–60° C. |
| 211 | 4-[2-(4-chlorophenyl)ethoxy]quinoline | 106–107° C. |
| 212 | 8-fluoro-4-[2-(4-methylphenyl)ethoxy]quinoline | 89–90° C. |
| 213 | 4-(1-methyl-2-phenylethoxy)quinoline | oil |
| 214 | 8-fluoro-4-[1-(phenylmethyl)ethoxy]quinoline | oil |
| 215 | 8-bromo-4-[2-(4-chlorophenyl)ethoxy]quinoline | 112–114° C. |
| 216 | 8-chloro-4-[2-(2-chlorophenyl)ethoxy]quinoline | 90–92° C. |
| 217 | 8-fluoro-4-[2-(2-(1-methylethyl)phenyl)ethoxy]quinoline | oil |
| 218 | 8-fluoro-4-[2-(3-(phenylthio)phenyl)ethoxy]quinoline | oil |
| 219 | 8-fluoro-4-(2-phenylethoxy)quinoline | 63–65° C. |
| 220 | 4-(2-phenylpropoxy)-8-fluoroquinoline | oil |
| 221 | 4-[2-[4-(t-butyl)phenyl]ethoxy]-8-fluoroquinoline | 81–82° C. |
| 222 | 8-fluoro-4-[2-(4-fluorophenyl)ethoxy]quinoline | 126–127° C. |
| 223 | 4-[2-(4-bromophenyl)ethoxy]-8-fluoroquinoline | 130° C. |
| 224 | 8-fluoro-4-[2-(3-methylphenyl)ethoxy]quinoline | 92° C. |
| 225 | 8-fluoro-4-[2-(2-fluorophenyl)ethoxy]quinoline | 75° C. |
| 226 | 7-chloro-4-[2-(4-chlorophenyl)ethoxy]quinoline | 96–97° C. |
| 227 | 8-fluoro-4-[2-(2,4,6-trimethylphenyl)ethoxy]quinoline | |
| 228 | 8-fluoro-4-[2-(2-methoxyphenyl)ethoxy]quinoline | 74–75° C. |
| 229 | 4-[2-(2-methoxyphenyl)ethoxy]quinoline | oil |
| 230 | 7-chloro-4-[2-(1,1'-biphenyl)-4-yl-ethoxy]quinoline | 95–96° C. |
| 231 | 7-chloro-4-[2-(4-(t-butyl)phenyl)ethoxy]quinoline | 123–124° C. |
| 232 | 4-[2-(4-(t-butyl)phenyl)ethoxy]-7-fluoroquinoline | 98–99° C. |
| 233 | 4-[2-(1,1'-biphenyl)-4-ylethoxy]-7-fluoroquinoline | 73–75° C. |
| 234 | 4-[2-(4-chlorophenyl)ethoxy]-7-fluoroquinoline | 81–82° C. |
| 235 | 7-fluoro-4-[2-(4-methylphenyl)ethoxy]quinoline | 85–86° C. |

TABLE 7-continued

4-(2-phenylethoxy)quinolines

| EXAMPLE NUMBER | COMPOUND | M.P. |
|---|---|---|
| 236 | 7-chloro-4-[2-(4-fluorophenyl)ethoxy]-quinoline | 80° C. |
| 237 | 8-fluoro-4-[2-(1,1'-biphenyl)-2-yl-ethoxy]quinoline | 55–60° C. |
| 238 | 8-fluoro-4-[2-(4-(i-propyl)phenyl)-ethoxy]quinoline | 59–60° C. |
| 239 | 4-(2-phenylethoxy)-7-(trifluoromethyl)quinoline | 55–57° C. |
| 240 | 8-chloro-4-[2-(4-fluorophenyl)-ethoxy]quinoline | 125–127° C. |

TABLE 8

4-(3-phenylpropoxy)quinolines

| EXAMPLE NUMBER | COMPOUND | M.P. |
|---|---|---|
| 241 | 8-fluoro-4-[3-(4-(t-butyl)phenyl]-propoxy]quinoline | 103–105° C. |
| 242 | 8-chloro-4-[3-(4-chlorophenyl)-propoxy]quinoline | 117–119° C. |
| 243 | 8-fluoro-4-[(3-phenyl-2-propenyl)-oxy]quinoline | 128–130° C. |

TABLE 9

4-(2-Arylethoxy)quinolines

| EXAMPLE NUMBER | COMPOUND | M.P. |
|---|---|---|
| 244 | 8-fluoro-4-[2-(1-naphthyl)-ethoxy]quinoline | 121–122° C. |
| 245 | 4-[2-(2-thienyl)ethoxy]-quinoline | oil |
| 246 | 8-fluoro-4-[2-(2-thienyl)-ethoxy]quinoline | 77–79° C. |
| 247 | 8-fluoro-4-[2-(2-naphthyl)ethoxy]-quinoline | 123–124° C. |
| 248 | 5-chloro-4-(2-cyclohexylethoxy)-2,8-dimethylquinoline | 100–102° C. |
| 249 | 6-fluoro-4-(2-cyclohexylethoxy)-2-methylquinoline | 113–115° C. |

TABLE 10

Bis(2-phenylethoxy)quinolines

| EXAMPLE NUMBER | COMPOUND | M.P. |
|---|---|---|
| 250 | 8-fluoro-2,4-bis[2-(4-methylphenyl)ethoxy]quinoline | 125–126° C. |
| 251 | 4,8-bis[2-(4-methylphenyl)ethoxy]-quinoline | 142–143° C. |

TABLE 11

4-(3-Arylpropyl)quinolines

| EXAMPLE NUMBER | COMPOUND | M.P. |
|---|---|---|
| 252 | 4-(3-phenylpropyl)quinoline | |
| 253 | 8-fluoro-4-(3-phenylpropyl)quinoline | 43–45° C. |
| 254 | 4-(3-phenylpropyl)-7-(trifluoromethyl)quinoline | oil |
| 255 | 8-chloro-4-(3-phenylpropyl)quinoline | 70–71° C. |
| 256 | 8-fluoro-4-[3-(4-(i-propyl)phenyl)-propyl]quinoline | oil |
| 257 | 4-[3-(1,1'-biphenyl)-4-ylpropyl]-8-fluoroquinoline | oil |
| 258 | 8-fluoro-4-[3-(4-methylphenyl)propyl)]-quinoline | oil |
| 259 | 8-fluoro-4-[3-(3-(trifluoromethyl)-phenyl]propyl]quinoline | 65–66° C. |
| 260 | 4-[3-[4-(t-butyl)phenyl]propyl]-8-fluoroquinoline | oil |

TABLE 11-continued

4-(3-Arylpropyl)quinolines

| EXAMPLE NUMBER | COMPOUND | M.P. |
|---|---|---|
| 261 | 4-[3-(4-chlorophenyl)propyl]-8-fluoroquinoline | 97° C. |

TABLE 12

Additional Compounds

| EXAMPLE NUMBER | COMPOUND | M.P. |
|---|---|---|
| 262 | 4-[2-[4-(t-butyl)phenyl]ethoxy]-quinoline | 67–69° C. |
| 263 | 8-fluoro-4-[2-(1,1'-biphenyl)-4-yl-ethoxy]quinoline | 97–99° C. |
| 264 | 8-fluoro-4-[(2-phenylethyl)sulfinyl]-quinoline | NA |
| 265 | 8-fluoro-4-[2-[4-(2-hydroxyethyl)-phenyl]ethoxy]quinoline | NA |
| 266 | 8-fluoro-4-[3-methoxybutoxy]-quinoline | oil |
| 267 | 8-fluoro-4-(4-pentenoxy)quinoline | 75–78° C. |
| 268 | 8-fluoro-N-(4-phenylbutyl)-4-quinolinamine | 104–106° C. |
| 269 | 4-[2-(2-chlorophenyl)ethoxy]-8-fluoroquinoline | 78–80° C. |
| 270 | 4-[2-[1,1'-biphenyl]-4-ylbutoxy]-8-fluoroquinoline | oil |
| 271 | N-[3-[4-(t-butyl)phenyl]propyl]-8-fluoro-4-quinolinamine | oil |
| 272 | 8-fluoro-4-(4-phenoxybutoxy)quinoline | 87–89° C. |
| 273 | N-[2-(4-acetoxyphenyl)ethyl]-N-(8-fluoro-4-quinolinyl)acetamide | oil |
| 274 | 8-fluoro-4-(3,5,5-trimethylhexyloxy)-quinoline | oil |
| 275 | 8-fluoro-4-[2-(2,4-difluorophenyl)-ethoxy]quinoline | 98–100° C. |
| 276 | 7-chloro-4-[2-(2,4-difluorophenyl)-ethoxy]quinoline | 103–105° C. |
| 277 | 5,7-dichloro-4-[2-(4-ethoxyphenyl)-ethoxy]quinoline | 104–105° C. |
| 278 | 4-[2-(4-butoxyphenyl)ethoxy]-8-fluoroquinoline | 80–82° C. |
| 279 | 6-ethoxy-2-methyl-4-[3-(phenylmethoxy)propoxy]quinoline | 38–40° C. |
| 280 | 8-chloro-N-[2-(3-phenoxyphenyl)-ethyl]-4-quinolinamine | 145–147° C. |
| 281 | 8-chloro-N-(4-phenylbutyl)-4-quinolinamine | 134–136° C. |
| 282 | 8-fluoro-4-[3-(4-phenoxyphenyl)propoxy]quinoline | 94–96° C. |
| 283 | 7-chloro-N-[2-(4-chlorophenyl)-propyl]-4-quinolinamine | 145–147° C. |
| 284 | 4-[(4,5-dibromopentyl)oxy]-8-fluoroquinoline | 70–73° C. |
| 285 | 8-fluoro-4-[(8-phenoxyoctyl)-oxy]quinoline | 80–81° C. |
| 286 | 6-chloro-2-methyl-4-[2-[4-(t-butyl)-phenyl]ethoxy]quinoline | 83–86° C. |
| 287 | 8-fluoro-4-[(6-phenoxyhexyl)oxy]-quinoline | NA |
| 288 | 8-chloro-N-(2-methyl-2-phenylpropyl)-4-quinolinamine | 137–139° C. |
| 289 | 8-fluoro-N-(2-methyl-2-phenylpropyl)-4-quinolinamine | 136–138° C. |
| 290 | 6-methoxy-2-methyl-N-[2-(3-phenoxyphenyl)ethyl]-4-quinolinamine | NA |
| 291 | 8-fluoro-N-[2-[4-(phenylmethoxy)-phenyl]ethyl]-4-quinolinamine | 157–159° C. |
| 292 | 7-fluoro-4-[2-(4-bromophenoxy)-ethoxy]quinoline | 127–129° C. |
| 293 | N-[2-(4-hydroxyphenyl)ethyl]-8-fluoro-4-quinoline | 249–251° C. |
| 294 | 8-fluoro-4-[3-[3-(trifluoromethyl)-phenyl]propoxy]quinoline | 67–69° C. |
| 295 | 8-fluoro-4-(2-phenylcyclohexyloxy)-quinoline | NA |
| 296 | 8-chloro-N-[2-(2,4-difluorophenyl)- | 206–208° C. |

TABLE 12-continued

Additional Compounds

| EXAMPLE NUMBER | COMPOUND | M.P. |
|---|---|---|
| | ethyl]-4-quinolinamine | |
| 297 | 8-fluoro-4-[2-[4-(1,1,2,2-tetra-fluoroethoxy)phenyl]ethoxy]quinoline | 70–72° C. |
| 298 | N-[2-[3,4-bis(phenylmethoxy)-phenyl]ethyl]-8-fluoro-4-quinolinamine | 137–139° C. |
| 299 | 4-[2-(6-chloro-1,3-benzodioxol-5-yl)-ethoxy]-8-fluoroquinoline | 143–145° C. |
| 300 | 8-fluoro-N-[2-(4-ethoxyphenyl)ethyl]-4-quinolinamine | 179–181° C. |
| 301 | N-[2-(4-ethoxyphenyl)ethyl]-4-quinolinamine | 125–126° C. |
| 302 | 8-fluoro-4-[3-(4-ethoxyphenyl)propyl]-quinoline | oil |
| 303 | 4-[3-(4-ethoxyphenyl)propyl]quinoline | oil |
| 304 | 8-fluoro-4-[3-(4-methoxyphenyl)-propyl]quinoline | oil |
| 305 | 8-fluoro-4-(2,2-dimethylbutoxy)-quinoline | oil |
| 306 | 8-fluoro-N-[2-[4-(butoxy)phenyl]-ethyl]-4-quinolinamine | 118–120° C. |
| 307 | 7-[(8-fluoro-4-quinolinyl)oxy]-heptanenitrile | 94–96° C. |
| 308 | 8-fluoro-4-[2-(3,4-difluorophenyl)-ethoxy]quinoline | 87–89° C. |
| 309 | 8-fluoro-4-[2-(1,3-benzodioxol-5-yl)ethoxy]quinoline | 103–105° C. |
| 310 | 4-[2-(2,6-dichlorophenyl)ethoxy]-8-fluoroquinoline | 128–129° C. |
| 311 | 8-chloro-4-[2-(2-chloro-4-fluoro-phenyl)ethoxy]quinoline | 104–106° C. |
| 312 | 8-fluoro-N-[2-(3-methoxyphenyl)-ethyl]-4-quinolinamine | 153–155° C. |
| 313 | 8-fluoro-N-[2-(4-ethylphenyl)-ethyl]-4-quinolinamine | 162–164° C. |
| 314 | 8-fluoro-4-[2-[4-(heptyloxy)phenyl]-ethoxy]quinoline | 45–47° C. |
| 315 | (E)-8-fluoro-4-[(2-phenylethenyl)-oxy]quinoline | 99–101° C. |
| 316 | (Z)-8-fluoro-4-[(2-phenylethenyl)-oxy]quinoline | 95–97° C. |
| 317 | 8-fluoro-N-[2-[4-(propoxy)phenyl]-ethyl]-4-quinolinamine | 140–142° C. |
| 318 | 8-chloro-4-[2-(3,4-difluorophenyl)-ethoxy]quinoline | 84–86° C. |
| 319 | 4-[3-[4-(i-propyl)phenyl]propyl]-quinoline | oil |
| 320 | 7-chloro-4-[2-(1,3-benzodioxol-5-yl)-ethoxy]quinoline | 75–77° C. |
| 321 | 8-fluoro-4-[2-(4-methoxyphenoxy)-ethoxy]quinoline | 107–109° C. |
| 322 | 8-fluoro-4-[2-[4-(3-methylphenoxy)-phenyl]ethoxy]quinoline | 98–100° C. |
| 323 | 8-chloro-4-[2-(2,4-difluorophenyl)-ethoxy]quinoline | 118–120° C. |
| 324 | N-[2-(5-bromo-2-methoxyphenyl)ethyl]-8-fluoro-4-quinolinamine | 176–178° C. |
| 325 | 8-fluoro-4-[2-(4-propoxyphenyl)-ethoxy]quinoline | 108–110° C. |
| 326 | 8-fluoro-4-(2-phenoxyethoxy)quinoline | 118–120° C. |
| 327 | 8-fluoro-N-[4-[4-(trifluoromethyl)-phenyl]butyl]-4-quinolinamine | 110–112° C. |
| 328 | 8-fluoro-N-[2-[4-(1,1,2,2-tetra-fluoroethoxy)phenyl]ethyl]-4-quinolinamine | 168–170° C. |

The procedures described in the following detailed Examples are representative of the procedures used to prepare the compounds of the other Examples.

EXAMPLE 4

N-Ethyl-N-(2-phenylethyl)-4-quinolinamine

To a suspension of 0.59 g of lithium aluminum hydride in 100 mL of dry ether was added, dropwise, a solution of 2.3 g of N-(2-phenylethyl)-N-(4-quinolinyl)acetamide dissolved in 50 mL of dry ether. The mixture was heated to reflux for seven hours. Excess lithium aluminum hydride was then destroyed by adding 100 mL of water to the mixture. The solvent was then removed, and the residue was dissolved in chloroform. After washing with water, the mixture was then dried and concentrated. Using HPLC (silica gel, $CH_2Cl_2 \rightarrow EtOAc$), 0.80 g of the title product was isolated. Yield 36.7%. M.P. oil.

EXAMPLE 10

N-[2-(4-Chlorophenyl)ethyl]-N-[8-fluoro-4 quinolinyl)]acetamide

A mixture of 2.0 g of N-[2-(4-chlorophenyl)ethyl]-8-fluoro-4-quinolinamine and 5.0 mL of acetic anhydride was refluxed overnight. The mixture was then cooled, and solvents were removed by reducing pressure. The residue was washed with water and then dried. The resulting oil was passed over a silica gel column with ethyl acetate, and the front running spot was collected, producing 0.8 g of the title product as a thick oil.

EXAMPLE 25

2-Chloro-N-(2-phenylethyl)-4-quinolinamine

To 0.6 g of 2-hydroxy-N-(2-phenylethyl)-4-quinolinamine was added 15 mL of $POCl_3$. The mixture was heated to reflux overnight, then cooled and concentrated to dryness. A mixture of ammonium hydroxide in water was added, then the product was extracted into $CH_2Cl_2$. This solution was concentrated to dryness, and the product was recrystallized from pentane/$CH_2Cl_2$, giving 0.55 g of the title product. Yield 85.9%. M.P. 132°–133° C.

EXAMPLE 69

3-Chloro-N-(2-chloro-2-phenylethyl)-4-quinolinamine

A mixture of 4.1 g of 1-phenyl-2-(4-quinolinylamino)ethanol, 100 mL of $POCl_3$ and 6.5 g of $PCl_5$ was heated to reflux for 18 hours, then cooled and concentrated to dryness. An ice/water mixture was added, then the product was extracted into $CH_2Cl_2$. This solution was concentrated to dryness, and the residue was purified by HPLC (silica gel column eluted with pentane/$CH_2Cl_2$ (50:50)). Fractions containing the product were combined and concentrated to dryness producing 0.433 g of the title product. Yield 8.7%. M.P. oil.

EXAMPLE 97

8-Fluoro-N-[2-(2-trifluoromethyl)phenyl]-4-quinolinamine

To 2.0 g of 4-chloro-8-fluoroquinoline was added 4.1 g of 2-[2-(trifluoromethyl)phenyl]ethylamine. The mixture was stirred and heated to 160°–165° C. under nitrogen for two hours, then cooled, and 200 mL of a 50:50 mixture of ammonium hydroxide and water was added. The product was extracted into $CH_2Cl_2$, which was concentrated to dryness. Recrystallization from a pentane/$CH_2Cl_2$ mixture yielded 1.5 g of the title product. Yield 41.6%.

EXAMPLE 154

8-Fluoro-N-[2-(4-phenyl-2-thiazolyl)ethyl]-4-quinolinamine

To 1.0 g of 4-chloro-8-fluoroquinoline was added 2.6 g of 2-β-aminoethyl-4-phenylthiazole monohydrochloride. The mixture was stirred under nitrogen and heated to 170°–175° C. for one hour. The mixture was then cooled and 250 mL of a 50:50 mixture of ammonium hydroxide and water was added. The product was extracted into $CH_2Cl_2$, which was then concentrated to dryness. Recrystallizing from pentane/$CH_2Cl_2$ gave 0.410 g of the title product. Yield 21.6%. M.P. 134°–135° C.

EXAMPLE 159

8-Fluoro-N-[2-(2-naphthyl)ethyl]-4-quinolinamine

A mixture of 2.0 g of 4-chloro-8-fluoroquinoline and 3.8 g of 2-(2-naphthyl)ethyl amine was heated under nitrogen to 160°–165° C. for one hour. Then 200 mL of a 50:50 mixture of ammonium hydroxide in water was added. The product was extracted from the mixture into $CH_2Cl_2$, which was then concentrated to dryness. The residue was recrystallized from pentane/ethyl acetate to give 1.4 g of the title product. Yield 41.2%. M.P. 173°–174° C.

EXAMPLE 173

8-Fluoro-N-[2-(2-thienyl)ethyl]-4-quinolinamine

A mixture of 2.0 g of 4-chloro-8-fluoroquinoline and 2.8 g of 2-(2-thienyl)ethyl amine was heated under nitrogen to 160°–165° C. for two hours, then cooled and combined with 200 mL of a 50:50 mixture of ammonium hydroxide and water. The product was extracted into $CH_2Cl_2$, which was then concentrated to dryness. The residue was recrystallized from pentane/$CH_2Cl_2$ to give 1.0 g of the title product. Yield 34.5%. M.P. 157°–158° C.

EXAMPLE 181

Bis[2-phenylethyl]-2,4-quinolinediamine

To 2.0 g of 2,4-dichloroquinoline was added 4.8 g of 2-phenylethylamine, and the mixture was heated to 150°–160° C. under nitrogen for 18 hours. The mixture was then cooled and a solution of ammonium hydroxide and water was added. The product was extracted into $CH_2Cl_2$, which was then concentrated to dryness, giving an oil. To the oil, 100 mL of pentane and $CH_2Cl_2$ was added and the oil went into solution. This solution was cooled, and the title product crystallized. Yield 44.4%. M.P. 70°–71° C.

EXAMPLE 186

N,N'-Bis[2-(4-chlorophenyl)ethyl]-2,7-quinolinediamine

A mixture of 2.0 g of 4-chloro-7-fluoroquinoline and 3.5 g of 2-(4-chlorophenyl)ethyl amine was heated neat until fuming began. The mixture was then cooled. The product was extracted into a $CHCl_3$/ammonium hydroxide solution, which was then washed with water. Solvent was removed by reducing pressure. The residue was placed on a silica gel column with acetone, then flushed with ethanol. Solvent was removed by reducing pressure, giving the title product as a yellow-brown foam. Yield 1.1 g. M.P. 55°–60° C.

EXAMPLE 209

4-[2-(4-Chlorophenyl)ethoxy]-8-fluoroquinoline

To 1.2 g of sodium hydride in 50 mL of DMF was added 3.9 g of 2-(4-chlorophenyl)ethyl alcohol. The mixture was stirred at room temperature for one hour, then 4.5 g of 4-chloro-8-fluoroquinoline in 10 mL of DMF was added, the mixture was heated to reflux for two hours. Then the mixture was allowed to cool to room temperature while it was stirred for four hours, after which it was poured into an ice/water mixture. The mixture was filtered, and the filter cake was washed with $H_2O$. Recrystallization from pentane/ethyl acetate gave 0.840 g of the title product. Yield 11.2%. M.P. 139°–140° C.

EXAMPLE 221

4-[2-[4-(t-Butyl)phenyl]ethoxy]-8-fluoroquinoline

To a mixture of 1.1 g of sodium hydride in 50 mL of DMF was added 4.0 g of 2-[4-(1,1-dimethylethyl)phenyl]ethyl alcohol, and the mixture was stirred for one hour at room temperature. Then 4.0 g of 4-chloro-8fluoroquinoline in 20 mL of DMF were added, and the mixture was stirred at room temperature overnight. Then the mixture was poured into an ice/water mixture, and the solid was collected and recrystallized from ethyl acetate/pentane to give 2.3 g of the title product. Yield 32.4%. M.P. 81°–82° C.

EXAMPLE 238

8-Fluoro-4-[2-[4-(i-propyl)phenyl]ethoxyquinoline

To a suspension of 0.96 g of sodium hydride in 10 mL of dry DMF was added 3.6 g of 4-chloro-8-fluoroquinoline. The mixture was cooled in an ice/water bath, and 3.3 g of 2-[4-(1-methylethyl)phenyl]ethyl alcohol was added. The mixture was stirred overnight, then diluted with ice and water. The pH was adjusted to 7, then the product was extracted into $CH_2Cl_2$. The $CH_2Cl_2$ layer was separated, filtered, and evaporated in vacuo. An azeotrope with xylene was formed to facilitate removal of residual DMF. The residue was chromatographically purified on a silica gel column, eluting with $CH_2Cl_2$, →5% EtOAc/$CH_2Cl_2$ →10% EtOAc/$CH_2Cl_2$. The fractions containing product were combined and evaporated to give an oil, which crystallized on adding ether. Recrystallization yielded 2.5 g of title product. M.P. 56°–60° C.

EXAMPLES 212 and 251

8-fluoro-4-[2-(4-methylphenyl)ethoxy]quinoline, 4,8-Bis[2-(4-methylphenyl)ethoxy]quinoline To a solution of 1.2 g of sodium hydride in 50 ml of DMF was added 3.4 g of 2-(4-methylphenyl)ethanol, and the mixture was stirred for one hour at room temperature. Then 4.5 g of 4-chloro-8-fluoroquinoline were added, the mixture was heated to reflux for five hours, and then cooled to room temperature, and poured into a mixture of ice in water. The solid phase was collected and dried. TLC showed three products. These were separated by HPLC (silica gel, 70% pentane/30% EtOAc) giving 1.84 g of 8-fluoro-4-[2-(4-methylphenyl)ethoxy]quinoline (Yield: 26.3%; M.P. 89°–90° C.) 0.610 g of 4-chloro-8-[2-(4-methylphenyl)ethoxy]quinoline (Yield: 8.7%; M.P. 74°–75° C.); and 0.450 g of 4,8-bis[2-(4-methylphenyl)ethoxy]quinoline (Yield: 6.4%; M.P. 142°–143° C).

EXAMPLE 261

4-[3-(4-chlorophenyl)propyl]-8-fluoroquinoline

A mixture of 3.63 g of 4-chloroquinoline and 5.3 g of 5-[2-(4-chlorophenyl)ethyl]barbituric acid was heated to 150° C. for 1¼ hours, to form 5-[2-(4-chlorophenyl)ethyl]-5-(4-quinolinyl)barbituric acid. This compound was hydrolyzed, without isolation, by adding 4 g of NaOH in 40 ml of water and refluxing for four hours. The mixture was cooled, acidified with HCl and refluxed for several hours, cooled, and neutralized with dilute NaOH. The desired product was extracted into $CH_2Cl_2$, which was then filtered through phase separating paper and evaporated to dryness. The residue was absorbed onto silica gel and chromatographed over silica gel using $CH_2Cl_2$. Fractions containing product were combined to give 2.69 g of crystalline material. This was recrystallized from a petroleum ether/$CH_2Cl_2$ mixture to give 2.35 g of the title product. Yield: 39%. M.P. 97° C.

Utility

Plant Pathology

The compounds of the present invention have been found to control fungi, particularly plant pathogens. When employed in the treatment of plant fungal diseases, the compounds are applied to the plants in a disease inhibiting and "phytologically acceptable amount". The term "disease inhibiting" and "phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. The compounds of the invention may also be used to protect stored grain and other nonplant loci from fungal infestation.

Greenhouse Tests

The following experiments were performed in the laboratory, to determine the fungicidal efficacy of the compounds of the invention.

Test 1

This screen was used to evaluate the efficacy of the present compounds against a variety of different organisms that cause plant diseases.

The test compounds were formulated for application by dissolving 50 mg of the compound into 1.25 ml of solvent. The solvent was prepared by mixing 50 ml of "Tween 20" with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Tables | Host |
|---|---|---|
| Erysiphe graminis tritici (powdery mildew) | POWD MDEW | wheat |
| Pyricularia oryzae (rice blast) | RICE BLAS | rice |
| Puccinia recondita tritici (leaf rust) | LEAF RUST | wheat |
| Botrytis cinerea (gray mold) | GRAY MOLD | grape berries |
| Pseudoperonospora cubensis (downy mildew) | DOWN MDEW | squash |
| Cercospora beticola (leaf spot) | LEAF SPOT | sugar beet |
| Venturia inaequalis (apple scab) | APPL SCAB | apple seedling |
| Septoria tritici (leaf blotch) | LEAF BLOT | wheat |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2-4 hours.

The effectiveness of test compounds in controlling disease was rated on the following scale:

| | |
|---|---|
| 0 = | not tested against specific organism |
| − = | 0-19% control at 400 ppm |
| + = | 20-89% control at 400 ppm |
| + + = | 90-100% control at 400 ppm |
| + + + = | 90-100% control at 400 ppm. |

Table 13 gives the results.

TABLE 13

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 1 | + | + | + | + | + + | 0 | − | − |
| 2 | − | − | − | − | + + + | 0 | − | − |
| 3 | − | + + | + | − | + + + | 0 | − | − |
| 4 | + | + | + + | − | + + | 0 | − | − |
| 5 | + + | + + | + + + | − | + + + | 0 | − | + + + |
| 6 | + + | + | + | + | + + | 0 | − | − |
| 7 | + | + | + + + | − | + + + | − | − | + + + |
| 8 | + | + + | + | − | + + + | + + + | − | + |
| 9 | + | + | + | − | + + + | − | − | − |
| 10 | + + | + + + | + + + | − | + + | + + + | − | + + + |
| 11 | − | + + | + + + | − | + + | + + + | − | − |
| 12 | + | + + | + + + | − | + + | + + + | − | + + |
| 13 | − | + + | + + | − | + + | − | − | − |
| 14 | − | + | + | − | + + + | + + + | − | − |
| 15 | − | + | + | − | + + + | + + + | + | − |
| 16 | − | + | + | − | + + + | + + + | − | − |
| 17 | + + | + | + + | − | + + | 0 | − | − |
| 18 | + | + + | + + | + | + + | 0 | − | − |
| 19 | + | + + | + + | − | + + + | 0 | − | − |
| 20 | + | + | + | − | + + + | 0 | − | − |
| 21 | + | + | + | − | + + | 0 | − | − |
| 22 | + | + | + | − | + + + | 0 | − | − |
| 23 | + | + | + | − | + + + | 0 | − | − |

TABLE 13-continued

| EX. NO. | POW'D MDEW | RICE BLAST | LEAF RUST | GRAY MOLD | DOWN MDEW | LEAF SPOT | APPL SCAB | LEAF BLOT |
|---|---|---|---|---|---|---|---|---|
| 24 | + | + | + | − | +++ | 0 | − | − |
| 25 | + | + | ++ | − | +++ | 0 | − | − |
| 26 | + | + | − | − | +++ | 0 | − | − |
| 27 | + | ++ | + | − | +++ | 0 | − | − |
| 28 | + | ++ | + | − | +++ | 0 | − | − |
| 29 | − | + | + | − | − | 0 | 0 | 0 |
| 30 | − | + | + | − | +++ | 0 | − | − |
| 31 | ++ | + | + | − | +++ | 0 | − | − |
| 32 | + | + | − | − | +++ | 0 | − | − |
| 33 | − | + | + | − | +++ | 0 | − | − |
| 34 | + | + | ++ | − | +++ | + | − | − |
| 35 | + | + | + | − | +++ | +++ | − | − |
| 36 | + | +++ | +++ | − | +++ | +++ | − | +++ |
| 37 | + | − | + | − | + | 0 | 0 | 0 |
| 38 | + | − | ++ | − | +++ | + | − | − |
| 39 | +++ | +++ | +++ | − | +++ | 0 | 0 | 0 |
| 40 | − | ++ | +++ | − | + | 0 | 0 | 0 |
| 41 | + | ++ | +++ | − | ++ | +++ | − | + |
| 42 | +++ | + | ++ | − | +++ | +++ | − | − |
| 43 | + | + | − | − | ++ | +++ | − | − |
| 44 | +++ | + | + | − | +++ | +++ | + | − |
| 45 | + | ++ | + | − | ++ | +++ | − | − |
| 46 | + | ++ | + | − | ++ | +++ | + | + |
| 47 | + | − | + | − | + | 0 | 0 | 0 |
| 48 | + | + | + | − | ++ | + | − | − |
| 49 | − | + | + | − | + | 0 | 0 | 0 |
| 50 | +++ | − | ++ | − | +++ | − | − | − |
| 51 | − | + | + | − | +++ | +++ | − | − |
| 52 | − | + | + | − | +++ | + | − | +++ |
| 53 | +++ | + | + | − | +++ | +++ | − | + |
| 54 | − | ++ | + | − | +++ | +++ | − | + |
| 55 | + | ++ | + | − | ++ | +++ | − | − |
| 56 | − | ++ | ++ | − | +++ | +++ | − | + |
| 57 | − | ++ | + | − | ++ | +++ | − | − |
| 58 | − | − | + | − | +++ | 0 | 0 | 0 |
| 59 | + | + | − | − | − | 0 | 0 | 0 |
| 60 | ++ | +++ | ++ | − | +++ | 0 | 0 | 0 |
| 61 | − | ++ | ++ | − | +++ | 0 | 0 | 0 |
| 62 | − | ++ | ++ | − | +++ | − | − | + |
| 63 | − | + | +++ | − | ++ | 0 | 0 | 0 |
| 64 | + | − | + | − | +++ | 0 | 0 | 0 |
| 65 | + | + | ++ | − | +++ | − | − | + |
| 66 | + | ++ | +++ | − | +++ | +++ | − | + |
| 67 | − | + | + | − | ++ | + | − | − |
| 68 | + | + | +++ | − | ++ | − | − | +++ |
| 69 | + | + | + | − | +++ | − | − | − |
| 70 | +++ | + | + | − | − | − | − | − |
| 71 | + | + | +++ | − | +++ | +++ | − | + |
| 72 | ++ | +++ | +++ | − | +++ | 0 | 0 | 0 |
| 73 | − | + | − | − | ++ | − | − | − |
| 74 | + | + | +++ | − | +++ | +++ | − | − |
| 75 | + | + | ++ | − | +++ | − | − | + |
| 76 | ++ | +++ | +++ | − | +++ | − | + | +++ |
| 77 | + | + | ++ | − | +++ | − | + | − |
| 78 | + | ++ | +++ | − | +++ | +++ | − | + |
| 79 | + | ++ | ++ | − | +++ | +++ | − | + |
| 80 | + | ++ | ++ | − | +++ | + | − | − |
| 81 | + | ++ | ++ | − | +++ | + | − | − |
| 82 | + | +++ | +++ | − | +++ | + | − | +++ |
| 83 | + | ++ | +++ | +++ | ++ | + | − | − |
| 84 | +++ | ++ | ++ | − | ++ | + | − | − |
| 85 | − | − | + | − | − | 0 | 0 | 0 |
| 86 | − | − | + | − | + | 0 | 0 | 0 |
| 87 | − | − | + | − | +++ | − | − | − |
| 88 | − | − | ++ | − | ++ | + | − | − |
| 89 | − | − | + | − | +++ | 0 | 0 | 0 |
| 90 | − | +++ | +++ | − | +++ | 0 | 0 | 0 |
| 91 | + | + | − | − | ++ | − | − | − |
| 92 | + | ++ | +++ | − | ++ | + | − | +++ |
| 93 | − | − | − | − | − | + | − | + |
| 94 | + | +++ | +++ | − | +++ | +++ | − | + |
| 95 | + | ++ | +++ | + | +++ | + | + | +++ |
| 96 | + | +++ | +++ | − | +++ | +++ | − | +++ |
| 97 | + | +++ | +++ | − | +++ | +++ | − | +++ |
| 98 | − | + | ++ | − | ++ | − | − | − |
| 99 | − | ++ | +++ | − | +++. | + | − | − |
| 100 | + | + | + | − | + | 0 | 0 | 0 |
| 101 | +++ | − | + | − | +++ | +++ | + | − |
| 102 | + | + | − | − | − | 0 | 0 | 0 |
| 103 | + | ++ | ++ | − | +++ | + | +++ | + |

TABLE 13-continued

| EX. NO. | POW'D MDEW | RICE BLAST | LEAF RUST | GRAY MOLD | DOWN MDEW | LEAF SPOT | APPL SCAB | LEAF BLOT |
|---|---|---|---|---|---|---|---|---|
| 104 | − | − | − | − | ++ | + | + | − |
| 105 | +++ | ++ | +++ | − | +++ | + | − | + |
| 106 | ++ | + | + | − | + | + | − | + |
| 107 | ++ | + | + | − | +++ | − | − | − |
| 108 | + | + | ++ | − | + | − | − | +++ |
| 109 | + | + | ++ | − | +++ | 0 | 0 | 0 |
| 110 | − | + | ++ | − | ++ | 0 | 0 | 0 |
| 111 | + | ++ | +++ | − | +++ | − | − | +++ |
| 112 | − | − | + | − | +++ | − | − | − |
| 113 | + | +++ | +++ | − | +++ | − | − | +++ |
| 114 | +++ | +++ | +++ | − | +++ | +++ | − | +++ |
| 115 | − | + | − | − | + | 0 | 0 | 0 |
| 116 | − | + | +++ | − | +++ | + | + | − |
| 117 | + | + | + | − | +++ | + | − | − |
| 118 | − | + | − | − | − | − | − | − |
| 119 | + | + | + | − | ++ | − | + | + |
| 120 | − | + | + | − | ++ | +++ | − | − |
| 121 | + | − | ++ | − | + | 0 | 0 | 0 |
| 122 | − | ++ | + | − | ++ | − | − | − |
| 123 | − | + | + | − | +++ | − | − | − |
| 124 | +++ | + | + | − | − | − | − | − |
| 125 | + | − | − | − | − | 0 | 0 | 0 |
| 126 | ++ | ++ | + | − | + | − | − | + |
| 127 | + | + | + | − | + | 0 | 0 | 0 |
| 128 | − | + | + | − | − | 0 | 0 | 0 |
| 129 | − | + | ++ | − | + | − | + | − |
| 130 | − | − | − | − | − | 0 | 0 | 0 |
| 131 | − | − | − | − | + | 0 | 0 | 0 |
| 132 | − | − | − | − | − | 0 | 0 | 0 |
| 133 | − | + | + | − | + | 0 | 0 | 0 |
| 134 | + | ++ | + | − | +++ | 0 | 0 | 0 |
| 135 | − | − | − | − | +++ | − | − | + |
| 136 | + | − | − | − | +++ | − | − | − |
| 137 | + | +++ | + | − | +++ | 0 | 0 | 0 |
| 138 | − | + | + | − | +++ | 0 | 0 | 0 |
| 139 | − | + | + | − | ++ | − | − | − |
| 140 | + | +++ | +++ | − | +++ | +++ | + | +++ |
| 141 | − | ++ | + | − | + | 0 | 0 | 0 |
| 142 | − | ++ | ++ | − | +++ | 0 | 0 | 0 |
| 143 | ++ | ++ | +++ | − | +++ | + | − | + |
| 144 | − | + | ++ | − | +++ | + | + | − |
| 145 | − | + | + | − | +++ | + | − | − |
| 146 | − | − | − | − | + | 0 | 0 | 0 |
| 147 | − | + | + | − | +++ | − | − | − |
| 148 | − | + | + | − | ++ | + | − | − |
| 149 | + | + | ++ | − | ++ | +++ | − | + |
| 150 | + | + | ++ | − | ++ | +++ | − | +++ |
| 151 | + | + | ++ | − | +++ | + | − | + |
| 152 | ++ | +++ | ++ | − | +++ | +++ | − | +++ |
| 153 | + | ++ | ++ | − | + | − | − | − |
| 154 | ++ | + | +++ | − | +++ | + | + | + |
| 155 | − | + | − | − | +++ | − | − | − |
| 156 | − | + | + | − | +++ | − | − | − |
| 157 | − | ++ | ++ | − | +++ | 0 | 0 | 0 |
| 158 | + | +++ | +++ | − | +++ | + | − | +++ |
| 159 | ++ | +++ | +++ | − | +++ | + | − | +++ |
| 160 | − | + | − | − | − | 0 | 0 | 0 |
| 161 | + | + | − | − | + | 0 | 0 | 0 |
| 162 | + | + | ++ | − | +++ | − | − | − |
| 163 | ++ | + | +++ | − | ++ | +++ | − | − |
| 164 | − | + | + | + | ++ | + | − | − |
| 165 | + | ++ | ++ | − | +++ | +++ | + | − |
| 166 | + | + | + | − | +++ | − | − | + |
| 167 | + | − | − | − | + | 0 | 0 | 0 |
| 168 | + | ++ | ++ | − | +++ | − | − | − |
| 169 | + | ++ | + | − | ++ | − | − | − |
| 170 | + | + | ++ | − | + | − | − | − |
| 171 | − | + | + | − | + | + | − | + |
| 172 | + | + | + | − | + | − | − | − |
| 173 | + | + | ++ | − | +++ | +++ | − | + |
| 174 | + | + | ++ | − | +++ | − | − | + |
| 175 | + | + | +++ | − | +++ | − | − | + |
| 176 | + | + | + | − | ++ | + | − | − |
| 177 | ++ | +++ | +++ | − | +++ | 0 | 0 | 0 |
| 178 | − | + | ++ | − | +++ | 0 | 0 | 0 |
| 179 | − | − | − | − | ++ | + | + | − |
| 180 | ++ | + | − | − | ++ | + | − | + |
| 181 | + | + | + | − | +++ | 0 | 0 | 0 |
| 182 | − | + | − | − | − | 0 | 0 | 0 |
| 183 | − | ++ | ++ | − | +++ | + | + | − |

TABLE 13-continued

| EX. NO. | POWD MDEW | RICE BLAST | LEAF RUST | GRAY MOLD | DOWN MDEW | LEAF SPOT | APPL SCAB | LEAF BLOT |
|---|---|---|---|---|---|---|---|---|
| 184 | − | + | ++ | − | ++ | − | − | − |
| 185 | − | + | + | − | + | 0 | 0 | 0 |
| 186 | − | − | + | − | +++ | + | − | + |
| 187 | − | + | + | − | +++ | − | − | − |
| 188 | − | ++ | + | − | ++ | 0 | 0 | 0 |
| 189 | − | + | + | − | + | − | − | − |
| 190 | − | + | +++ | − | − | − | − | − |
| 191 | − | + | ++ | − | − | 0 | 0 | 0 |
| 192 | − | − | ++ | − | +++ | − | − | + |
| 193 | − | − | + | − | − | 0 | 0 | 0 |
| 194 | + | − | − | − | − | 0 | 0 | 0 |
| 195 | +++ | +++ | +++ | − | +++ | 0 | 0 | 0 |
| 196 | +++ | +++ | +++ | − | +++ | 0 | 0 | 0 |
| 197 | +++ | +++ | +++ | − | + | 0 | 0 | 0 |
| 198 | − | − | − | − | − | 0 | 0 | 0 |
| 199 | ++ | ++ | +++ | − | +++ | 0 | 0 | 0 |
| 200 | +++ | +++ | +++ | − | + | + | + | +++ |
| 201 | +++ | + | +++ | − | +++ | +++ | + | +++ |
| 202 | +++ | + | ++ | − | ++ | + | − | + |
| 203 | + | +++ | +++ | − | ++ | + | + | ++ |
| 204 | + | − | + | − | + | 0 | 0 | 0 |
| 205 | ++ | +++ | +++ | − | +++ | 0 | 0 | 0 |
| 206 | +++ | +++ | +++ | − | +++ | 0 | 0 | 0 |
| 207 | ++ | +++ | +++ | − | +++ | + | + | +++ |
| 208 | ++ | +++ | +++ | − | +++ | + | − | + |
| 209 | +++ | +++ | +++ | − | +++ | +++ | + | +++ |
| 210 | ++ | +++ | +++ | − | +++ | + | − | +++ |
| 211 | ++ | +++ | +++ | − | +++ | +++ | − | +++ |
| 212 | ++ | +++ | +++ | − | +++ | − | +++ | +++ |
| 213 | + | ++ | ++ | − | +++ | − | + | + |
| 214 | + | +++ | + | − | ++ | 0 | 0 | 0 |
| 215 | − | + | + | − | ++ | 0 | 0 | 0 |
| 216 | ++ | ++ | ++ | − | ++ | 0 | 0 | 0 |
| 217 | +++ | +++ | +++ | − | −−+ | 0 | 0 | 0 |
| 218 | +++ | +++ | +++ | − | +++ | 0 | 0 | 0 |
| 219 | ++ | +++ | +++ | − | +++ | + | + | + |
| 220 | ++ | + | ++ | − | ++ | − | + | − |
| 221 | + | − | +++ | − | +++ | +++ | + | +++ |
| 222 | + | + | +++ | − | +++ | + | +++ | +++ |
| 223 | ++ | +++ | +++ | − | − | 0 | 0 | 0 |
| 224 | ++ | +++ | +++ | − | +++ | 0 | 0 | 0 |
| 225 | ++ | +++ | +++ | − | +++ | 0 | 0 | 0 |
| 226 | + | − | + | − | + | 0 | 0 | 0 |
| 227 | − | + | + | − | − | 0 | 0 | 0 |
| 228 | ++ | +++ | +++ | − | +++ | + | +++ | +++ |
| 229 | + | +++ | ++ | − | +++ | − | − | + |
| 230 | ++ | − | + | − | − | − | − | − |
| 231 | + | − | − | − | − | 0 | 0 | 0 |
| 232 | − | − | − | − | − | 0 | 0 | 0 |
| 233 | + | ++ | ++ | − | + | − | − | + |
| 234 | + | + | ++ | − | + | + | − | + |
| 235 | + | ++ | ++ | − | + | − | − | + |
| 236 | +++ | − | + | − | − | − | − | − |
| 237 | ++ | ++ | + | − | − | 0 | 0 | 0 |
| 238 | +++ | +++ | +++ | + | ++ | 0 | 0 | 0 |
| 239 | +++ | ++ | ++ | − | ++ | 0 | 0 | 0 |
| 240 | − | + | ++ | − | − | 0 | 0 | 0 |
| 241 | − | − | − | − | − | 0 | 0 | 0 |
| 242 | − | − | − | − | − | 0 | 0 | 0 |
| 243 | − | − | − | − | − | 0 | 0 | 0 |
| 244 | + | ++ | + | − | + | − | − | + |
| 245 | + | ++ | ++ | − | ++ | − | − | − |
| 246 | ++ | +++ | +++ | − | +++ | + | +++ | +++ |
| 247 | ++ | +++ | +++ | − | + | − | − | +++ |
| 248 | + | − | − | − | − | 0 | 0 | 0 |
| 249 | − | − | − | − | − | 0 | 0 | 0 |
| 250 | − | − | + | − | + | 0 | 0 | 0 |
| 251 | − | + | − | − | + | − | − | − |
| 252 | ++ | ++ | +++ | − | ++ | − | + | + |
| 253 | +++ | ++ | +++ | − | ++ | + | +++ | + |
| 254 | ++ | ++ | − | − | − | 0 | 0 | 0 |
| 255 | + | +++ | +++ | − | + | 0 | 0 | 0 |
| 256 | +++ | +++ | +++ | − | ++ | 0 | 0 | 0 |
| 257 | +++ | + | +++ | − | +++ | 0 | 0 | 0 |
| 258 | ++ | +++ | ++ | − | ++ | + | − | + |
| 259 | + | +++ | +++ | + | +++ | − | +++ | +++ |
| 260 | ++ | +++ | +++ | − | +++ | + | − | +++ |
| 261 | + | + | + | − | + | − | + | 0 |
| 262 | − | ++ | +++ | − | +++ | 0 | 0 | 0 |
| 263 | + | + | + | − | − | 0 | 0 | 0 |

TABLE 13-continued

| EX. NO. | POW'D MDEW | RICE BLAST | LEAF RUST | GRAY MOLD | DOWN MDEW | LEAF SPOT | APPL SCAB | LEAF BLOT |
|---|---|---|---|---|---|---|---|---|
| 264 | − | − | + | − | 0 | 0 | 0 | 0 |
| 265 | − | ++ | ++ | − | − | 0 | 0 | 0 |
| 266 | − | − | − | − | − | 0 | 0 | 0 |
| 267 | ++ | +++ | ++ | − | + | 0 | 0 | 0 |
| 268 | + | +++ | +++ | − | +++ | 0 | 0 | 0 |
| 269 | ++ | +++ | +++ | − | +++ | 0 | 0 | 0 |
| 270 | − | + | − | − | − | 0 | 0 | 0 |
| 271 | − | +++ | + | − | +++ | 0 | 0 | 0 |
| 272 | − | + | − | − | + | 0 | 0 | 0 |
| 273 | + | ++ | + | − | + | 0 | 0 | 0 |
| 274 | ++ | ++ | ++ | − | + | 0 | 0 | 0 |
| 275 | +++ | +++ | +++ | − | +++ | 0 | 0 | 0 |
| 276 | +++ | − | + | − | − | 0 | 0 | 0 |
| 277 | ++ | − | − | − | − | 0 | 0 | 0 |
| 278 | +++ | +++ | +++ | − | +++ | 0 | 0 | 0 |
| 279 | − | ++ | ++ | − | ++ | 0 | 0 | 0 |
| 280 | +++ | +++ | +++ | − | +++ | 0 | 0 | 0 |
| 281 | + | +++ | + | − | +++ | 0 | 0 | 0 |
| 282 | − | + | − | − | − | 0 | 0 | 0 |
| 283 | + | + | ++ | − | ++ | 0 | 0 | 0 |
| 284 | − | +++ | ++ | − | + | 0 | 0 | 0 |
| 285 | − | − | − | − | − | 0 | 0 | 0 |
| 286 | + | − | + | − | − | 0 | 0 | 0 |
| 287 | − | − | + | − | ++ | 0 | 0 | 0 |
| 288 | − | + | − | − | + | 0 | 0 | 0 |
| 289 | + | ++ | ++ | − | +++ | 0 | 0 | 0 |
| 290 | − | +++ | + | − | +++ | 0 | 0 | 0 |
| 291 | +++ | +++ | +++ | − | +++ | 0 | 0 | 0 |
| 292 | − | − | − | − | − | 0 | 0 | 0 |
| 293 | − | − | ++ | − | − | 0 | 0 | 0 |
| 294 | − | − | − | − | − | 0 | 0 | 0 |
| 295 | + | + | + | − | ++ | 0 | 0 | 0 |
| 296 | − | ++ | ++ | − | + | 0 | 0 | 0 |
| 297 | +++ | ++ | +++ | − | +++ | 0 | 0 | 0 |
| 298 | − | − | − | − | − | 0 | 0 | 0 |
| 299 | + | ++ | +++ | − | ++ | 0 | 0 | 0 |
| 300 | + | +++ | +++ | − | +++ | 0 | 0 | 0 |
| 301 | − | − | +++ | − | +++ | 0 | 0 | 0 |
| 302 | +++ | +++ | +++ | − | +++ | 0 | 0 | 0 |
| 303 | +++ | +++ | +++ | − | +++ | 0 | 0 | 0 |
| 304 | + | +++ | +++ | − | +++ | 0 | 0 | 0 |
| 305 | + | + | − | − | + | 0 | 0 | 0 |
| 306 | + | +++ | +++ | − | +++ | 0 | 0 | 0 |
| 307 | − | − | − | − | − | 0 | 0 | 0 |
| 308 | + | +++ | +++ | − | +++ | 0 | 0 | 0 |
| 309 | + | +++ | +++ | − | +++ | 0 | 0 | 0 |
| 310 | − | ++ | − | − | − | 0 | 0 | 0 |
| 311 | + | − | ++ | − | ++ | 0 | 0 | 0 |
| 312 | ++ | − | +++ | − | +++ | 0 | 0 | 0 |
| 317 | ++ | +++ | +++ | − | +++ | 0 | 0 | 0 |
| 318 | − | ++ | ++ | − | − | 0 | 0 | 0 |
| 319 | +++ | +++ | +++ | − | ++ | 0 | 0 | 0 |
| 320 | + | + | ++ | − | + | 0 | 0 | 0 |
| 321 | − | + | ++ | − | − | 0 | 0 | 0 |
| 322 | +++ | +++ | +++ | − | + | 0 | 0 | 0 |
| 323 | + | ++ | +++ | − | − | 0 | 0 | 0 |
| 324 | − | − | + | − | + | 0 | 0 | 0 |
| 325 | ++ | ++ | +++ | − | +++ | 0 | 0 | 0 |
| 326 | − | + | + | − | − | 0 | 0 | 0 |
| 327 | +++ | − | ++ | − | +++ | 0 | 0 | 0 |
| 328 | + | − | +++ | − | +++ | 0 | 0 | 0 |

Field Tests

Selected compounds were field tested against a variety of plant pathogens. The following table reports pathogens against which compounds of the invention showed activity in these tests.

TABLE 14

| COMPOUND EX. NO. | CROP | PATHOGEN |
|---|---|---|
| 2 | barley | Pyrenophora teres |
|  | potato | Phytophthora infestans |
|  | tomato | Phytophthora infestans |
| 5 | barley | Pyrenophora teres |
|  |  | Rhynchosporium secalis |

TABLE 14-continued

| COMPOUND EX. NO. | CROP | PATHOGEN |
|---|---|---|
|  | cucumber | Sphaerotheca fuliginea |
|  | grape | Plasmopara viticola |
|  | potato | Phytophthora infestans |
|  | rape | Alternaria brassica |
|  | tomato | Phytophthora infestans |
| 10 | barley | Rhynchosporium secalis |
|  |  | Pyrenophora teres |
|  |  | Erysiphe graminis hordei |
|  | cucumber | Sphaerotheca fuliginea |
|  | wheat | Pseudocercosporella herpotrichoides |
|  |  | Erysiphe graminis tritici |

TABLE 14-continued

| COMPOUND EX. NO. | CROP | PATHOGEN |
|---|---|---|
| 97 | grape | *Plasmopara viticola* |
| 159 | barley | *Rhynchosporium secalis* |
|  | grape | *Plasmopara viticola* |
|  | wheat | *Puccinia recondita* |
| 173 | grape | *Plasmopara viticola* |
| 200 | barley | *Rhynchosporium secalis* |
|  |  | *Pyrenophora teres* |
|  |  | *Erysiphe graminis hordei* |
|  | cucumber | *Sphaerotheca fuliginea* |
|  | wheat | *Pseudocercosporella herpotrichoides* |
|  |  | *Erysiphe graminis tritici* |
| 212 | apple | *Podosphaera leucotricha* |
|  | barley | *Pyrenophora teres* |
|  | grape | *Uncinula necator* |
|  |  | *Plasmopara viticola* |
|  | rape | *Alternaria brassica* |
|  | rice | *Piricularia oryzae* |
| 212 | barley | *Rhynchosporium secalis* |
|  |  | *Pyrenophora teres* |
|  |  | *Erysiphe graminis hordei* |
|  | cucumber | *Sphaerotheca fuliginea* |
|  | wheat | *Pseudocercosporella herpotrichoides* |
|  |  | *Erysiphe graminis tritici* |
| 219 | barley | *Rhynchosporium secalis* |
|  |  | *Pyrenophora teres* |
|  |  | *Erysiphe graminis hordei* |
|  | cucumber | *Sphaerotheca fuliginea* |
|  | wheat | *Pseudocercosporella herpotrichoides* |
|  |  | *Erysiphe graminis tritici* |
| 221 | sugar beet | *Erysiphe* sp. |

Combinations

Fungal disease pathogens are known to develop resistance to fungicides. When strains resistant to a fungicide do develop, it becomes necessary to apply larger and larger amounts of the fungicide to obtain desired results. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (1) in combination with a second fungicide.

Contemplated classes of fungicides from which the second fungicide may be selected include:

(1) N-substituted azoles, for example propiconazole, triademefon, flusilazol, diniconazole, ethyltrianol, myclobutanil, and prochloraz;

(2) pyrimidines, such as fenarimol and nuarimol;

(3) morpholines, such as fenpropimorph and tridemorph;

(4) piperazines, such as triforine; and (5) pyridines, such as pyrifenox. Fungicides in these five classes all function by inhibiting sterol biosynthesis. Additional classes of contemplated fungicides, which have other mechanisms of action, include:

(6) dithiocarbamates, such as maneb and mancozeb;

(7) phthalimides, such as captafol;

(8) isophthalonitrites, such as chlorothalonil;

(9) dicarboximides, such as iprodione;

(10) benzimidazoles, such as benomyl and carbendazim;

(11) 2-aminopyrimidines, such as ethirimol;

(12) carboxamides, such as carboxin; and

(13) dinitrophenols, such as dinocap.

The fungicide combinations of the invention contain at least 1%, ordinarily 20 to 80%, and more typically 50 to 75% by weight of a compound of formula (1).

Combination Tests

Selected compounds were tested in the greenhouse in combination with other known fungicides against various plant pathogens. Results are reported in Tables 15 and 16. In the tables, the time given under "Time in hours" is the number of hours elapsing between treatment and inoculation. A negative time indicates that the pathogen was inoculated before treatment. In such cases, curative activity was being tested. A positive time indicates that the plants were treated before they were inoculated with pathogen. In such cases, residual or protectant activity was tested. The compounds were formulated and applied as foliar sprays as in Test 1. The results were evaluated on a 1-9 rating scale. These ratings represent the following percent disease control: 1=0-19%, 2=20-29%, 3=30-39%, 4=40-59%, 5 6=75-89%, 7=90-96%, 8=97-99%, and 9=100%.

TABLE 15

CUCURBIT DOWNY MILDEW

| COMPOUND 1 PLUS COMPOUND 2 | TIME IN HOURS | RATE CMPD 1 IN PPM | RATE CMPD 2 IN PPM | RESULTS |
|---|---|---|---|---|
| Ex. 5 | 4 | 48.00 |  | 8.0 |
|  |  | 24.00 |  | 7.5 |
|  |  | 12.00 |  | 7.0 |
|  |  | 6.00 |  | 1.0 |
| nuarimol | 4 | 2.00 |  | 1.0 |
|  |  | 1.00 |  | 1.0 |
|  |  | 0.50 |  | 1.0 |
|  |  | 0.25 |  | 1.0 |
| nuarimol + Ex. 5 | 4 | 2.00 | 48.00 | 8.5 |
|  |  | 1.00 | 24.00 | 7.5 |
|  |  | 0.50 | 12.00 | 5.0 |
|  |  | 0.25 | 6.00 | 1.0 |

TABLE 16

CUCURBIT POWDERY MILDEW

| Ex. 5 | 4 | 48.00 |  | 6.0 |
|---|---|---|---|---|
|  |  | 24.00 |  | 5.0 |
|  |  | 12.00 |  | 1.0 |
|  |  | 6.00 |  | 1.0 |
| nuarimol | 4 | 2.00 |  | 9.0 |
|  |  | 1.00 |  | 8.0 |
|  |  | 0.50 |  | 7.0 |
|  |  | 0.25 |  | 6.0 |
| nuarimol + Ex. 5 | 4 | 2.00 | 48.00 | 9.0 |
|  |  | 1.00 | 24.00 | 9.0 |
|  |  | 0.50 | 12.00 | 8.0 |
|  |  | 0.25 | 6.00 | 6.0 |

Insecticide and Miticide Utility

The compounds of the invention are also useful for the control of insects and mites. Therefore, the present invention also is directed to a method for inhibiting an insect or mite which comprises applying to a locus of the insect or mite an insect- or mite-inhibiting amount of a compound of formula (1).

The compounds of the invention show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm.

Representative mite species with which it is contemplated that the present invention can be practiced include those listed below.

| FAMILY | SCIENTIFIC NAME | COMMON NAME |
|---|---|---|
| ACARIDAE | | |
| | *Aleurobius farinae* | |
| | *Rhizoglyphus echinopus* | Bulb mite |
| | *Rhizoglyphus elongatus* | |
| | *Rhizoglyphus rhizophagus* | |
| | *Rhizoglyphus sagittatae* | |
| | *Rhizoglyphus tarsalis* | |
| ERIOPHYIDAE | | |
| | *Abacarus farinae* | Grain rust mite |
| | *Aceria brachytarsus* | |
| | *Acalitus essigi* | Redberry mite |
| | *Aceria ficus* | |
| | *Aceria fraaxinivorus* | |
| | *Aceria granati* | |
| | *Aceria parapopuli* | |
| | *Eriophyes sheldoni* | Citrus bud mite |
| | *Aceria tulipae* | |
| | *Aculus carnutus* | Peach silver mite |
| | *Aculus schlechtendali* | Apple rust mite |
| | *Colomerus vitis* | Grape erineum mite |
| | *Eriophyes convolvens* | |
| | *Eriophyes insidiosus* | |
| | *Eriophyes malifoliae* | |
| | *Eriophyes padi* | |
| | *Eriophyes pruni* | |
| | *Epitrimerus pyri* | Pear leaf blister mite |
| | *Eriophyes ramosus* | |
| | *Eriophyes sheldoni* | Citrus bud mite |
| | *Eriophyes ribis* | |
| | *Phyllocoptes gracilis* | Dryberry mite |
| | *Phyllocoptruta oleivora* | Citrus rust mite |
| | *Phytoptus ribis* | |
| | *Trisetacus pini* | |
| | *Vasates amygdalina* | |
| | *Vasates eurynotus* | |
| | *Vasates quadripedes* | Maple balddergall mite |
| | *Vasates schlechtendali* | |
| EUPODIDAE | | |
| | *Penthaleus major* | Winter grain mite |
| | *Linopodes spp.* | |
| NALEPELLIDAE | | |
| | *Phylocoptella avellanae* | Filbert bud mite |
| PENTHALEIDAE | | |
| | *Halotydeus destrustor* | |
| PYEMOTIDAE | | |
| | *Pyemotes tritici* | Straw itch mite |
| | *Siteroptes cerealium* | |
| TARSONEMIDAE | | |
| | *Polyphagotarsonemus latus* | Broad mite |
| | *Steneotarsonemus pallidus* | Cyclamen mite |
| TENUIPALPIDAE | | |
| | *Brevipalpus californicus* | |
| | *Brevipalpus obovatus* | Privet mite |
| | *Brevipalpus lewisi* | Citrus flat mite |
| | *Dolichotetranychus floridanus* | Pineapple flase spider mite |
| | *Tenuipalpes granati* | |
| | *Tenuipalpes pacificus* | |
| TETRANYCHIDAE | | |
| | *Bryobia arborea* | |
| | *Bryobia practiosa* | Clover mite |
| | *Bryobia rubrioculus* | Brown mite |
| | *Eotetranychus coryli* | |
| | *Eotetranychus hicoriae* | Pecan deaf scorch mite |
| | *Eotetranychus lewisi* | |
| | *Eotetranychus sexmaculatus* | Sixspotted spider mite |
| | *Eotetranychus willametti* | |
| | *Eotetranychus banksi* | Texas citrus mite |
| | *Oligonychus ilicis* | Southern red mite |
| | *Oligonychus pratensis* | Banks grass mite |

| FAMILY | SCIENTIFIC NAME | COMMON NAME |
|---|---|---|
| | Oligonychus ununguis | Spruce spider mite |
| | Panonychus citri | Citrus red mite |
| | Panonychus ulmi | European red mite |
| | Paratetranychus modestus | |
| | Paratetranychus pratensis | |
| | Paratetranychus viridis | |
| | Petrobia latens | Brown wheat mite |
| | Schizotetranychus celarius | |
| | Bamboo spider mite | |
| | Schizotetranychus pratensis | |
| | Tetranychus canadensis | Fourspotted spider mite |
| | Tetranychus cinnabarinus | Carmine spider mite |
| | Tetranychus mcdanieli | McDaniel spider mite |
| | Tetranychus pacificus | Pacific spider mite |
| | Tetranychus schoenei | Schoene spider mite |
| | Tetranychus urticae | Twospotted spider mite |
| | Tetranychus turkestani | Strawberry spider mite |
| | Tetranychus desertorum | Desert spider mite |

The compounds are useful for reducing populations of insects and mites, and are used in a method of inhibiting an insect or mite population which comprises applying to a locus of the insect or arachnid an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts, which the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites; or a decrease in the number of viable insect or mite eggs. The extent of reduction accomplished by a compound depends, of course, upon the application rate of the compound, the particular compound used, and the target insect or mite species. At least an insectinactivating or mite-inactivating amount should be used. The terms "insect-inactivating amount" and "miteinactivating amount" are used to describe the amount, which is sufficient to cause a measurable reduction in the treated insect or mite population. Generally an amount in the range from about 1 to about 1000 ppm active compound is used.

In a preferred embodiment, the present invention is directed to a method for inhibiting a mite which comprises applying to a plant an effective miteinactivating amount of a compound of formula (1) in accordance with the present invention.

MITE/INSECT SCREEN

The compounds of Examples 1-295 were tested for miticidal and insecticidal activity in the following mite/insect screen.

Each test compound was formulated by dissolving the compound in acetone/alcohol (50:50) mixture containing 23 g of "TOXIMUL R" (sulfonate/nonionic emulsifier blend) and 13 g of "TOXIMUL S" (sulfonate/nonionic emulsifier blend) per liter. These mixtures were then diluted with water to give the indicated concentrations.

Twospotted spider mites (*Tetranychus urticae* Koch) and melon aphids (*Aphis gossypii* Glover) were introduced on squash cotyledons and allowed to establish on both leaf surfaces. Other plants in the same treatment pot were left uninfested. The leaves were then sprayed with 5 ml of test solution using a DeVilbiss atomizing sprayer at 10 psi. Both surfaces of the leaves were covered until runoff, and then allowed to dry for one hour. Two uninfested leaves were then excised and placed into a Petri dish containing southern armyworm (*Spodopetra eridania* Cramer).

After standard exposure periods, percent mortality was evaluated. Results are reported in Table 17, where the following abbreviations are used.

CRW refers to corn rootworm
SAW refers to Southern armyworm
SM refers to twospotted spider mites
MA refers to melon aphids.

TABLE 17

| | | | MITE/INSECT SCREEN | | | |
|---|---|---|---|---|---|---|
| COMPOUND EX. NO. | CRW RATE PPM | CRW RESULTS % | SAW SM & MA RATE PPM | SAW RESULTS % | SM RESULTS % | MA RESULTS % |
| 1 | 12.00 | 0 | 200 | 0 | 0 | 0 |
| 2 | 12.00 | 0 | 200 | 0 | 0 | 0 |
| 3 | 12.00 | 0 | 200 | 0 | 0 | 0 |
| 4 | 12.00 | 0 | 200 | 0 | 0 | 0 |
| 5 | 12.00 | 0 | 200 | 0 | 0 | 0 |
| 6 | 12.00 | 0 | 200 | 0 | 0 | 0 |
| 7 | 12.00 | 0 | 200 | 0 | 0 | 0 |
| 8 | 12.00 | 0 | 200 | 100 | 0 | 0 |
| 9 | 12.00 | 0 | 200 | 0 | 0 | 0 |
| 10 | 12.00 | 0 | 200 | 0 | 0 | 0 |
| | 24.00 | 0 | 400 | 0 | 0 | 0 |
| 11 | 24.00 | 60 | 400 | 100 | 0 | 0 |
| | 12.00 | 0 | 200 | 80 | 0 | 0 |
| 12 | 24.00 | 40 | 400 | 100 | 0 | 0 |

TABLE 17-continued

MITE/INSECT SCREEN

| COMPOUND EX. NO. | CRW RATE PPM | CRW RESULTS % | SAW SM & MA RATE PPM | SAW RESULTS % | SM RESULTS % | MA RESULTS % |
|---|---|---|---|---|---|---|
|  | 12.00 | 0 | 200 | 0 | 0 | 0 |
| 13 | 24.00 | 0 | 400 | 0 | 0 | 0 |
|  | 12.00 | 0 | 200 | 0 | 0 | 0 |
| 14 | 24.00 | 0 | 400 | 0 | 0 | 0 |
|  | 12.00 | 0 | 200 | 0 | 0 | 0 |
| 15 | 24.00 | 0 | 400 | 0 | 0 | 0 |
|  | 12.00 | 0 | 200 | 0 | 0 | 0 |
| 16 | 12.00 | 0 | 200 | 0 | 0 | 0 |
|  | 24.00 | 0 | 400 | 0 | 0 | 0 |
| 17 | 12.00 | 0 | 200 | 0 | 0 | 0 |
| 18 | 12.00 | 0 | 200 | 0 | 0 | 0 |
| 19 | 12.00 | 0 | 200 | 0 | 0 | 0 |
| 20 | 12.00 | 0 | 200 | 0 | 0 | 0 |
| 21 | 12.00 | 0 | 200 | 0 | 0 | 0 |
| 22 | 12.00 | 0 | 200 | 0 | 0 | 0 |
| 23 | 12.00 | 0 | 200 | 0 | 0 | 0 |
| 24 | 12.00 | 0 | 200 | 0 | 0 | 0 |
| 25 | 12.00 | 0 | 200 | 0 | 0 | 0 |
| 26 | 12.00 | 0 | 200 | 0 | 0 | 0 |
| 27 | 12.00 | 0 | 200 | 0 | 0 | 0 |
| 28 | 12.00 | 0 | 200 | 0 | 0 | 0 |
| 29 | 12.00 | 0 | 200 | 0 | 0 | 0 |
| 30 | 12.00 | 0 | 200 | 0 | 0 | 0 |
| 31 | 12.00 | 0 | 200 | 0 | 0 | 0 |
| 32 | 12.00 | 0 | 200 | 0 | 0 | 0 |
| 33 | 12.00 | 0 | 200 | 0 | 0 | 0 |
| 34 | 12.00 | 0 | 200 | 0 | 0 | 0 |
| 35 | 12.00 | 0 | 200 | 0 | 0 | 0 |
| 36 | 12.00 | 0 | 200 | 0 | 0 | 0 |
|  | 24.00 | 0 | 400 | 0 | 0 | 0 |
|  | 24.00 | 0 | 400 | 0 | 0 | 0 |
| 37 | 12.00 | 0 | 200 | 0 | 0 | 0 |
|  | 24.00 | 0 | 400 | 0 | 0 | 0 |
| 38 | 12.00 | 0 | 200 | 0 | 0 | 0 |
|  | 24.00 | 0 | 400 | 0 | 0 | 0 |
| 39 | 24.00 | 0 | 400 | 0 | 0 | 0 |
|  | 12.00 | 0 | 200 | 0 | 0 | 0 |
| 40 | 24.00 | 100 | 400 | 80 | 0 | 0 |
|  | 12.00 | 0 | 200 | 0 | 0 | 0 |
| 41 | 24.00 | 0 | 400 | 40 | 0 | 0 |
|  | 12.00 | 0 | 200 | 80 | 0 | 0 |
| 42 | 24.00 | 0 | 400 | 0 | 0 | 0 |
|  | 12.00 | 0 | 200 | 0 | 0 | 0 |
| 43 | 24.00 | 0 | 400 | 0 | 0 | 0 |
|  | 12.00 | 0 | 200 | 0 | 0 | 0 |
| 44 | 24.00 | 0 | 400 | 0 | 0 | 0 |
|  | 12.00 | 0 | 200 | 0 | 0 | 0 |
| 45 | 12.00 | 0 | 200 | 0 | 0 | 0 |
|  | 24.00 | 0 | 400 | 0 | 0 | 0 |
| 46 | 12.00 | 0 | 200 | 0 | 0 | 0 |
|  | 24.00 | 0 | 400 | 0 | 0 | 0 |
| 47 | 12.00 | 0 | 200 | 0 | 0 | 0 |
|  | 24.00 | 0 | 400 | 0 | 0 | 0 |
| 48 | 12.00 | 0 | 200 | 0 | 0 | 0 |
|  | 24.00 | 0 | 400 | 0 | 0 | 0 |
| 49 | 12.00 | 0 | 200 | 0 | 0 | 0 |
|  | 24.00 | 0 | 400 | 0 | 0 | 0 |
| 50 | 12.00 | 0 | 200 | 0 | 0 | 0 |
|  | 24.00 | 0 | 400 | 0 | 0 | 0 |
| 51 | 12.00 | 0 | 200 | 0 | 0 | 0 |
|  | 24.00 | 0 | 400 | 20 | 0 | 0 |
| 52 | 12.00 | 0 | 200 | 0 | 0 | 0 |
|  | 24.00 | 0 | 400 | 0 | 0 | 0 |
| 53 | 12.00 | 0 | 200 | 0 | 0 | 0 |
|  | 24.00 | 0 | 400 | 0 | 0 | 0 |
| 54 | 12.00 | 0 | 200 | 0 | 0 | 0 |
| 55 | 12.00 | 0 | 200 | 0 | 0 | 0 |
| 56 | 24.00 | 0 | 400 | 80 | 0 | 0 |
|  | 12.00 | 0 | 200 | 100 | 0 | 0 |
| 57 | 12.00 | 0 | 200 | 40 | 0 | 0 |
|  | 24.00 | 0 | 400 | 50 | 0 | 0 |
| 58 | 24.00 | 0 | 400 | 0 | 0 | 0 |
| 59 | 24.00 | 0 | 400 | 0 | 0 | 0 |
|  | 12.00 | 0 | 200 | 0 | 0 | 0 |
| 60 | 24.00 | 0 | 400 | 0 | 0 | 0 |
|  | 12.00 | 0 | 200 | 0 | 0 | 0 |
| 61 | 24.00 | 0 | 400 | 0 | 0 | 0 |
|  | 12.00 | 0 | 200 | 0 | 0 | 0 |

TABLE 17-continued

| | | | MITE/INSECT SCREEN | | | |
|---|---|---|---|---|---|---|
| COMPOUND EX. NO. | CRW RATE PPM | CRW RESULTS % | SAW SM & MA RATE PPM | SAW RESULTS % | SM RESULTS % | MA RESULTS % |
| 62 | 24.00 | 0 | 400 | 0 | 0 | 0 |
| 63 | 24.00 | 0 | 400 | 0 | 0 | 0 |
| 64 | 24.00 | 0 | 400 | 0 | 0 | 0 |
| | 12.00 | 0 | 200 | 60 | 0 | 0 |
| 65 | 12.00 | 0 | 200 | 0 | 0 | 0 |
| 66 | 12.00 | 0 | 200 | 0 | 0 | 0 |
| 67 | 12.00 | 0 | 200 | 0 | 0 | 0 |
| 68 | 12.00 | 0 | 200 | 0 | 0 | 0 |
| 69 | 12.00 | 0 | 200 | 0 | 0 | 0 |
| 70 | 12.00 | 0 | 200 | 0 | 0 | 0 |
| 71 | 12.00 | 0 | 200 | 0 | 0 | 0 |
| | 12.00 | 60 | 200 | 0 | 0 | 0 |
| 72 | 24.00 | 0 | 400 | 0 | 0 | 0 |
| 73 | 12.00 | 0 | 200 | 0 | 0 | 0 |
| 74 | 12.00 | 0 | 200 | 20 | 0 | 0 |
| | 12.00 | 0 | 200 | 0 | 0 | 0 |
| 75 | 12.00 | 0 | 200 | 0 | 0 | 0 |
| 76 | 12.00 | 0 | 200 | 0 | 0 | 0 |
| | 12.00 | 0 | 200 | 90 | 0 | 0 |
| 77 | 12.00 | 0 | 200 | 0 | 0 | 0 |
| 78 | 12.00 | 0 | 200 | 20 | 0 | 0 |
| | 12.00 | 0 | 200 | 20 | 0 | 0 |
| 79 | 12.00 | 0 | 200 | 10 | 0 | 0 |
| | 12.00 | 0 | 200 | 60 | 0 | 0 |
| 80 | 12.00 | 0 | 200 | 0 | 0 | 0 |
| 81 | 12.00 | 0 | 200 | 0 | 0 | 0 |
| 82 | 12.00 | 0 | 200 | 0 | 0 | 0 |
| 83 | 12.00 | 0 | 200 | 0 | 0 | 0 |
| 84 | 12.00 | 0 | 200 | 10 | 0 | 0 |
| | 24.00 | 0 | 400 | 0 | 0 | 0 |
| 85 | 12.00 | 0 | 200 | 0 | 0 | 0 |
| | 24.00 | 0 | 400 | 0 | 0 | 0 |
| 86 | 12.00 | 0 | 200 | 0 | 0 | 0 |
| | 24.00 | 0 | 400 | 0 | 0 | 0 |
| 87 | 12.00 | 0 | 200 | 0 | 0 | 0 |
| | 24.00 | 0 | 400 | 0 | 0 | 0 |
| 88 | 24.00 | 0 | 400 | 0 | 0 | 0 |
| | 12.00 | 0 | 200 | 0 | 0 | 0 |
| 89 | 24.00 | 0 | 400 | 0 | 0 | 0 |
| | 12.00 | 0 | 200 | 0 | 0 | 0 |
| 90 | 24.00 | 0 | 400 | 0 | 0 | 0 |
| | 12.00 | 0 | 200 | 100 | 80 | 80 |
| 91 | 12.00 | 0 | 200 | 0 | 0 | 0 |
| 92 | 12.00 | 0 | 200 | 0 | 0 | 0 |
| 93 | 12.00 | 0 | 200 | 0 | 0 | 0 |
| 94 | 12.00 | 100 | 200 | 0 | 0 | 0 |
| 95 | 12.00 | 0 | 200 | 20 | 0 | 0 |
| | 12.00 | 0 | 200 | 40 | 0 | 0 |
| 96 | 12.00 | 0 | 200 | 100 | 0 | 0 |
| | 12.00 | 0 | 200 | 100 | 0 | 0 |
| 97 | 12.00 | 0 | 200 | 0 | 0 | 0 |
| 98 | 12.00 | 0 | 200 | 0 | 0 | 0 |
| 99 | 12.00 | 0 | 200 | 0 | 0 | 0 |
| 100 | 12.00 | 0 | 200 | 0 | 0 | 0 |
| | 24.00 | 0 | 400 | 0 | 0 | 0 |
| 101 | 12.00 | 0 | 200 | 0 | 0 | 0 |
| | 24.00 | 0 | 400 | 0 | 0 | 0 |
| 102 | 12.00 | 0 | 200 | 0 | 0 | 0 |
| | 24.00 | 0 | 400 | 50 | 0 | 0 |
| 103 | 24.00 | 0 | 400 | 0 | 0 | 0 |
| | 12.00 | 0 | 200 | 0 | 0 | 0 |
| 104 | 12.00 | 0 | 200 | 0 | 0 | 0 |
| | 24.00 | 0 | 400 | 60 | 0 | 0 |
| 105 | 12.00 | 0 | 200 | 30 | 100 | 80 |
| | 24.00 | 0 | 400 | 0 | 0 | 50 |
| 106 | 24.00 | 0 | 400 | 0 | 0 | 0 |
| 107 | 24.00 | 0 | 400 | 0 | 0 | 0 |
| | 12.00 | 0 | 200 | 0 | 0 | 0 |
| 108 | 12.00 | 0 | 200 | 0 | 0 | 0 |
| 109 | 24.00 | 0 | 400 | 0 | 0 | 0 |
| 110 | 24.00 | 0 | 400 | 0 | 0 | 0 |
| | 12.00 | 0 | 200 | 0 | 0 | 0 |
| 111 | 12.00 | 0 | 200 | 20 | 90 | 0 |
| | 24.00 | 0 | 400 | 20 | 80 | 0 |
| 112 | 12.00 | 0 | 200 | 0 | 0 | 0 |
| | 24.00 | 0 | 400 | 0 | 0 | 0 |
| 113 | 12.00 | 0 | 200 | 100 | 40 | 0 |
| | 24.00 | 100 | 400 | 70 | 0 | 0 |

TABLE 17-continued

| COMPOUND EX. NO. | CRW RATE PPM | CRW RESULTS % | SAW SM & MA RATE PPM | SAW RESULTS % | SM RESULTS % | MA RESULTS % |
|---|---|---|---|---|---|---|
| 114 | 24.00 | 0 | 400 | 70 | 100 | 30 |
| 115 | 24.00 | 0 | 400 | 0 | 0 | 0 |
|  | 12.00 | 0 | 200 | 0 | 0 | 0 |
| 116 | 12.00 | 0 | 200 | 0 | 0 | 0 |
| 117 | 12.00 | 0 | 200 | 0 | 0 | 0 |
|  | 12.00 | 0 | 200 | 0 | 0 | 0 |
| 118 | 12.00 | 0 | 200 | 0 | 0 | 0 |
| 119 | 12.00 | 0 | 200 | 0 | 0 | 0 |
| 120 | 12.00 | 0 | 200 | 0 | 0 | 0 |
| 121 | 12.00 | 0 | 200 | 0 | 0 | 0 |
|  | 24.00 | 0 | 400 | 0 | 0 | 0 |
| 122 | 24.00 | 0 | 400 | 0 | 0 | 0 |
|  | 12.00 | 0 | 200 | 0 | 0 | 0 |
| 123 | 12.00 | 0 | 200 | 0 | 0 | 0 |
| 124 | 24.00 | 0 | 400 | 0 | 0 | 0 |
|  | 12.00 | 0 | 200 | 0 | 0 | 0 |
| 125 | 24.00 | 0 | 400 | 0 | 0 | 0 |
|  | 12.00 | 0 | 200 | 0 | 0 | 0 |
| 126 | 12.00 | 0 | 200 | 0 | 0 | 0 |
|  | 24.00 | 0 | 400 | 0 | 0 | 0 |
| 127 | 24.00 | 0 | 400 | 0 | 0 | 0 |
|  | 12.00 | 0 | 200 | 0 | 0 | 0 |
| 128 | 12.00 | 0 | 200 | 0 | 0 | 0 |
|  | 24.00 | 0 | 400 | 0 | 0 | 0 |
| 129 | 12.00 | 0 | 200 | 0 | 0 | 0 |
|  | 24.00 | 0 | 400 | 0 | 0 | 0 |
| 130 | 12.00 | 0 | 200 | 0 | 0 | 0 |
|  | 24.00 | 0 | 400 | 0 | 0 | 0 |
| 131 | 12.00 | 0 | 200 | 0 | 0 | 0 |
|  | 24.00 | 0 | 400 | 0 | 0 | 0 |
| 132 | 12.00 | 0 | 200 | 0 | 0 | 0 |
|  | 24.00 | 0 | 400 | 0 | 0 | 0 |
| 133 | 24.00 | 0 | 400 | 0 | 0 | 0 |
|  | 12.00 | 0 | 200 | 0 | 0 | 0 |
| 134 | 24.00 | 0 | 400 | 0 | 0 | 0 |
| 135 | 12.00 | 0 | 200 | 0 | 0 | 0 |
|  | 24.00 | 0 | 400 | 0 | 0 | 0 |
| 136 | 12.00 | 0 | 200 | 0 | 0 | 0 |
|  | 24.00 | 0 | 400 | 0 | 0 | 0 |
| 137 | 24.00 | 0 | 400 | 100 | 80 | 80 |
| 138 | 24.00 | 0 | 400 | 0 | 0 | 0 |
| 139 | 12.00 | 0 | 200 | 0 | 0 | 0 |
| 140 | 24.00 | 0 | 400 | 60 | 0 | 0 |
|  | 12.00 | 0 | 200 | 0 | 0 | 0 |
| 141 | 12.00 | 0 | 200 | 0 | 0 | 0 |
|  | 24.00 | 0 | 400 | 0 | 0 | 0 |
| 142 | 12.00 | 0 | 200 | 0 | 0 | 0 |
|  | 24.00 | 0 | 400 | 0 | 0 | 0 |
| 143 | 12.00 | 0 | 200 | 0 | 0 | 0 |
|  | 24.00 | 0 | 400 | 0 | 0 | 0 |
| 144 | 24.00 | 0 | 400 | 0 | 0 | 0 |
|  | 12.00 | 0 | 200 | 0 | 0 | 0 |
| 145 | 24.00 | 0 | 400 | 0 | 0 | 0 |
|  | 12.00 | 0 | 200 | 0 | 0 | 0 |
| 146 | 12.00 | 0 | 200 | 0 | 0 | 0 |
|  | 24.00 | 0 | 400 | 0 | 0 | 0 |
| 147 | 12.00 | 0 | 200 | 0 | 0 | 0 |
| 148 | 12.00 | 0 | 200 | 0 | 0 | 0 |
| 149 | 12.00 | 0 | 200 | 0 | 0 | 0 |
| 150 | 12.00 | 0 | 200 | 0 | 0 | 0 |
|  | 12.00 | 0 | 200 | 0 | 0 | 0 |
| 151 | 12.00 | 0 | 200 | 0 | 0 | 0 |
| 152 | 12.00 | 0 | 200 | 0 | 0 | 0 |
|  | 12.00 | 0 | 200 | 0 | 0 | 0 |
| 153 | 12.00 | 0 | 200 | 0 | 0 | 0 |
| 154 | 12.00 | 0 | 200 | 0 | 0 | 0 |
|  | 12.00 | 0 | 200 | 0 | 0 | 0 |
| 155 | 12.00 | 0 | 200 | 0 | 0 | 0 |
| 156 | 12.00 | 0 | 200 | 0 | 0 | 0 |
|  | 12.00 | 0 | 200 | 0 | 0 | 0 |
| 157 | 24.00 | 0 | 400 | 100 | 80 | 0 |
| 158 | 12.00 | 0 | 200 | 0 | 0 | 0 |
| 159 | 12.00 | 0 | 200 | 0 | 0 | 0 |
| 160 | 24.00 | 0 | 400 | 0 | 0 | 0 |
|  | 12.00 | 0 | 200 | 0 | 0 | 0 |
| 161 | 24.00 | 40 | 400 | 0 | 0 | 80 |
|  | 12.00 | 0 | 200 | 0 | 0 | 0 |
| 162 | 12.00 | 0 | 200 | 0 | 0 | 0 |

TABLE 17-continued

MITE/INSECT SCREEN

| COMPOUND EX. NO. | CRW RATE PPM | CRW RESULTS % | SAW SM & MA RATE PPM | SAW RESULTS % | SM RESULTS % | MA RESULTS % |
|---|---|---|---|---|---|---|
| 163 | 12.00 | 0 | 200 | 0 | 0 | 0 |
| 164 | 12.00 | 0 | 200 | 0 | 0 | 0 |
| 165 | 24.00 | 0 | 400 | 0 | 0 | 0 |
|  | 12.00 | 0 | 200 | 0 | 0 | 0 |
| 166 | 12.00 | 0 | 200 | 0 | 0 | 0 |
|  | 24.00 | 0 | 400 | 0 | 0 | 0 |
| 167 | 12.00 | 0 | 200 | 0 | 0 | 0 |
|  | 24.00 | 0 | 400 | 0 | 0 | 0 |
| 168 | 24.00 | 0 | 400 | 0 | 0 | 0 |
|  | 12.00 | 0 | 200 | 0 | 0 | 0 |
| 169 | 24.00 | 0 | 400 | 0 | 0 | 0 |
|  | 12.00 | 0 | 200 | 0 | 0 | 0 |
| 170 | 12.00 | 0 | 200 | 0 | 0 | 0 |
| 171 | 12.00 | 0 | 200 | 0 | 0 | 0 |
| 172 | 12.00 | 0 | 200 | 0 | 0 | 0 |
| 173 | 12.00 | 0 | 200 | 0 | 0 | 0 |
| 174 | 12.00 | 0 | 200 | 0 | 0 | 0 |
| 175 | 12.00 | 0 | 200 | 0 | 0 | 0 |
| 176 | 12.00 | 0 | 200 | 0 | 0 | 0 |
| 177 | 12.00 | 0 | 200 | 0 | 0 | 0 |
|  | 24.00 | 100 | 400 | 0 | 0 | 0 |
| 178 | 12.00 | 0 | 200 | 0 | 0 | 0 |
|  | 24.00 | 0 | 400 | 0 | 0 | 0 |
| 179 | 12.00 | 0 | 200 | 0 | 0 | 0 |
|  | 24.00 | 0 | 400 | 0 | 0 | 0 |
| 180 | 12.00 | 0 | 200 | 0 | 0 | 0 |
|  | 24.00 | 0 | 400 | 0 | 0 | 0 |
| 181 | 12.00 | 0 | 200 | 0 | 0 | 0 |
| 182 | 12.00 | 0 | 200 | 0 | 0 | 0 |
|  | 24.00 | 0 | 400 | 0 | 0 | 0 |
| 183 | 12.00 | 0 | 200 | 0 | 0 | 0 |
| 184 | 12.00 | 0 | 200 | 0 | 0 | 0 |
| 185 | 24.00 | 0 | 400 | 0 | 0 | 0 |
|  | 12.00 | 0 | 200 | 0 | 0 | 0 |
| 186 | 24.00 | 0 | 400 | 0 | 0 | 0 |
|  | 12.00 | 0 | 200 | 0 | 0 | 0 |
| 187 | 12.00 | 0 | 200 | 0 | 0 | 0 |
|  | 24.00 | 0 | 400 | 0 | 0 | 0 |
| 188 | 24.00 | 0 | 400 | 0 | 0 | 0 |
| 189 | 12.00 | 0 | 200 | 0 | 0 | 0 |
| 190 | 12.00 | 0 | 200 | 0 | 0 | 0 |
| 191 | 12.00 | 0 | 200 | 0 | 0 | 0 |
|  | 24.00 | 0 | 400 | 0 | 0 | 0 |
| 192 | 24.00 | 0 | 400 | 0 | 0 | 0 |
|  | 12.00 | 0 | 200 | 0 | 0 | 0 |
| 193 | 12.00 | 0 | 200 | 0 | 0 | 0 |
|  | 24.00 | 0 | 400 | 0 | 0 | 0 |
| 194 | 24.00 | 0 | 400 | 0 | 0 | 0 |
|  | 12.00 | 0 | 200 | 0 | 0 | 0 |
| 195 | 24.00 | 0 | 400 | 0 | 0 | 0 |
| 196 | 24.00 | 0 | 400 | 0 | 100 | 100 |
| 197 | 24.00 | 0 | 400 | 80 | 90 | 80 |
| 198 | 24.00 | 0 | 400 | 0 | 90 | 80 |
| 199 | 24.00 | 100 | 400 | 0 | 0 | 0 |
| 200 | 24.00 | 0 | 400 | 50 | 100 | 100 |
|  | 12.00 | 0 | 200 | 0 | 100 | 100 |
| 201 | 12.00 | 0 | 200 | 0 | 80 | 100 |
|  | 24.00 | 0 | 400 | 0 | 80 | 100 |
| 202 | 12.00 | 0 | 200 | 0 | 0 | 0 |
|  | 24.00 | 0 | 400 | 0 | 0 | 0 |
| 203 | 12.00 | 0 | 200 | 10 | 0 | 100 |
|  | 24.00 | 0 | 400 | 0 | 0 | 90 |
| 204 | 12.00 | 0 | 200 | 0 | 0 | 0 |
|  | 24.00 | 0 | 400 | 100 | 0 | 50 |
| 205 | 24.00 | 0 | 400 | 0 | 0 | 0 |
| 206 | 24.00 | 0 | 400 | 0 | 0 | 0 |
| 207 | 12.00 | 0 | 200 | 0 | 0 | 0 |
| 208 | 12.00 | 0 | 200 | 0 | 10 | 10 |
| 209 | 12.00 | 0 | 200 | 10 | 0 | 0 |
|  | 12.00 | 0 | 200 | 100 | 0 | 40 |
| 210 | 12.00 | 0 | 200 | 0 | 0 | 0 |
| 211 | 12.00 | 0 | 200 | 0 | 10 | 40 |
| 212 | 12.00 | 0 | 200 | 0 | 0 | 0 |
| 213 | 12.00 | 0 | 200 | 0 | 0 | 0 |
| 214 | 24.00 | 0 | 400 | 0 | 0 | 0 |
| 215 | 24.00 | 0 | 400 | 0 | 100 | 100 |
| 216 | 24.00 | 100 | 400 | 0 | 0 | 0 |
| 217 | 24.00 | 0 | 400 | 0 | 0 | 0 |

TABLE 17-continued

| | | MITE/INSECT SCREEN | | | | |
|---|---|---|---|---|---|---|
| COMPOUND EX. NO. | CRW RATE PPM | CRW RESULTS % | SAW SM & MA RATE PPM | SAW RESULTS % | SM RESULTS % | MA RESULTS % |
| 218 | 24.00 | 0 | 400 | 100 | 0 | 0 |
| 219 | 12.00 | 0 | 200 | 0 | 0 | 0 |
| 220 | 24.00 | 0 | 400 | 0 | 0 | 0 |
| | 12.00 | 0 | 200 | 0 | 0 | 0 |
| 221 | 24.00 | 0 | 400 | 0 | 90 | 80 |
| | 12.00 | 40 | 200 | 0 | 90 | 90 |
| 222 | 24.00 | 0 | 400 | 0 | 0 | 40 |
| | 12.00 | 0 | 200 | 0 | 0 | 50 |
| 223 | 24.00 | 0 | 400 | 0 | 0 | 100 |
| | 12.00 | 80 | 200 | 0 | 0 | 80 |
| 224 | 24.00 | 0 | 400 | 0 | 0 | 0 |
| 225 | 24.00 | 0 | 400 | 0 | 0 | 0 |
| 226 | 24.00 | 0 | 400 | 0 | 0 | 0 |
| | 12.00 | 0 | 200 | 0 | 0 | 0 |
| 227 | 12.00 | 0 | 200 | 0 | 0 | 0 |
| | 24.00 | 0 | 400 | 0 | 0 | 0 |
| 228 | 12.00 | 0 | 200 | 0 | 0 | 0 |
| | 24.00 | 0 | 400 | 0 | 0 | 80 |
| 229 | 12.00 | 0 | 200 | 0 | 50 | 50 |
| | 24.00 | 0 | 400 | 0 | 0 | 0 |
| 230 | 12.00 | 0 | 200 | 0 | 100 | 90 |
| | 24.00 | 0 | 400 | 0 | 80 | 0 |
| 231 | 12.00 | 0 | 200 | 0 | 90 | 0 |
| | 24.00 | 0 | 400 | 0 | 40 | 50 |
| 232 | 24.00 | 0 | 400 | 30 | 80 | 40 |
| | 12.00 | 0 | 200 | 0 | 100 | 70 |
| 233 | 12.00 | 0 | 200 | 0 | 100 | 50 |
| | 24.00 | 0 | 400 | 0 | 80 | 80 |
| 234 | 12.00 | 0 | 200 | 60 | 50 | 50 |
| | 24.00 | 0 | 400 | 0 | 30 | 100 |
| 235 | 24.00 | 0 | 400 | 0 | 0 | 50 |
| | 12.00 | 0 | 200 | 80 | 0 | 0 |
| 236 | 24.00 | 40 | 400 | 0 | 0 | 30 |
| | 12.00 | 0 | 200 | 0 | 0 | 0 |
| | 24.00 | 0 | 400 | 0 | 0 | 0 |
| 237 | 24.00 | 0 | 400 | 0 | 100 | 0 |
| | 12.00 | 0 | 200 | 0 | 0 | 0 |
| 238 | 24.00 | 0 | 400 | 100 | 0 | 0 |
| | 12.00 | 0 | 200 | 0 | 100 | 100 |
| 239 | 24.00 | 0 | 400 | 0 | 0 | 0 |
| | 12.00 | 0 | 200 | 0 | 0 | 0 |
| 240 | 24.00 | 0 | 400 | 0 | 0 | 0 |
| 241 | 24.00 | 0 | 400 | 0 | 0 | 0 |
| 242 | 24.00 | 0 | 400 | 0 | 0 | 0 |
| | 12.00 | 0 | 200 | 0 | 0 | 0 |
| 243 | 24.00 | 0 | 400 | 0 | 0 | 0 |
| 244 | 12.00 | 0 | 200 | 0 | 0 | 40 |
| 245 | 12.00 | 0 | 200 | 0 | 0 | 0 |
| 246 | 12.00 | 0 | 200 | 0 | 0 | 0 |
| 247 | 24.00 | 0 | 400 | 50 | 0 | 0 |
| | 12.00 | 0 | 200 | 20 | 90 | 0 |
| 248 | 24.00 | 0 | 400 | 0 | 0 | 0 |
| 249 | 24.00 | 0 | 400 | 0 | 0 | 0 |
| 250 | 24.00 | 0 | 400 | 0 | 0 | 0 |
| 251 | 12.00 | 0 | 200 | 0 | 0 | 0 |
| 252 | 24.00 | 0 | 400 | 0 | 90 | 100 |
| | 12.00 | 0 | 200 | 0 | 90 | 100 |
| 253 | 24.00 | 0 | 400 | 0 | 100 | 100 |
| | 12.00 | 0 | 200 | 0 | 100 | 90 |
| 254 | 24.00 | 0 | 400 | 0 | 0 | 0 |
| 255 | 24.00 | 0 | 400 | 0 | 0 | 0 |
| 256 | 24.00 | 100 | 400 | 100 | 0 | 0 |
| 257 | 24.00 | 0 | 400 | 0 | 0 | 0 |
| 258 | 24.00 | 0 | 400 | 0 | 90 | 100 |
| 259 | 24.00 | 0 | 400 | 0 | 80 | 80 |
| | 12.00 | 0 | 200 | 0 | 100 | 90 |
| 260 | 24.00 | 40 | 400 | 40 | 0 | 0 |
| | 12.00 | 0 | 200 | 100 | 100 | 100 |
| 261 | 24.00 | 100 | 400 | 80 | 50 | 100 |
| | 12.00 | 0 | 200 | 100 | 90 | 100 |
| 262 | 12.00 | 0 | 200 | 0 | 100 | 100 |
| | 24.00 | 0 | 400 | 0 | 100 | 100 |
| 263 | 12.00 | 0 | 200 | 0 | 0 | 0 |
| | 24.00 | 0 | 400 | 0 | 0 | 0 |
| 264 | 12.00 | 0 | 200 | 0 | 0 | 0 |
| | 24.00 | 0 | 400 | 0 | 0 | 0 |
| 265 | 12.00 | 0 | 200 | 0 | 0 | 0 |
| | 24.00 | 0 | 400 | 0 | 0 | 0 |

TABLE 17-continued

| | | | MITE/INSECT SCREEN | | | |
|---|---|---|---|---|---|---|
| COMPOUND EX. NO. | CRW RATE PPM | CRW RESULTS % | SAW SM & MA RATE PPM | SAW RESULTS % | SM RESULTS % | MA RESULTS % |
| 266 | 12.00 | 0 | 200 | 0 | 0 | 0 |
| | 24.00 | 0 | 400 | 0 | 0 | 0 |
| 267 | 12.00 | 0 | 200 | 0 | 40 | 20 |
| | 24.00 | 0 | 400 | 0 | 100 | 100 |
| 268 | 12.00 | 0 | 200 | 0 | 0 | 0 |
| | 24.00 | 0 | 400 | 0 | 80 | 0 |
| 269 | 12.00 | 0 | 200 | 0 | | 30 |
| | 24.00 | 40 | 400 | 0 | 0 | 0 |
| 270 | 12.00 | 0 | 200 | 20 | 0 | 0 |
| | 24.00 | 0 | 400 | 0 | 80 | 0 |
| 271 | 12.00 | 0 | 200 | 0 | 0 | 0 |
| | 24.00 | 0 | 400 | 0 | 0 | 0 |
| 272 | 12.00 | 0 | 200 | 0 | 0 | 0 |
| | 24.00 | 0 | 400 | 0 | 20 | 0 |
| 273 | 24.00 | 0 | 400 | 0 | 0 | 0 |
| 274 | 12.00 | 0 | 200 | 0 | 100 | 100 |
| | 24.00 | 0 | 400 | 0 | 0 | 100 |
| 275 | 12.00 | 0 | 200 | 0 | 0 | 90 |
| | 24.00 | 0 | 400 | 0 | 60 | 100 |
| 276 | 12.00 | 0 | 200 | 0 | 0 | 0 |
| | 24.00 | 0 | 400 | 0 | 60 | 80 |
| 277 | 24.00 | 0 | 400 | 0 | 0 | 0 |
| 278 | 12.00 | 0 | 200 | 0 | 60 | 90 |
| | 24.00 | 0 | 400 | 100 | 0 | 0 |
| 279 | 12.00 | 0 | 200 | 0 | 0 | 0 |
| | 24.00 | 0 | 400 | 0 | 0 | 80 |
| 280 | 12.00 | 0 | 200 | 60 | 0 | 0 |
| | 24.00 | 0 | 400 | 0 | 0 | 0 |
| 281 | 12.00 | 0 | 200 | 0 | 0 | 0 |
| | 24.00 | 0 | 400 | 0 | 0 | 0 |
| 282 | 12.00 | 0 | 200 | 0 | 0 | 0 |
| | 24.00 | 0 | 400 | 0 | 0 | 0 |
| 283 | 12.00 | 0 | 200 | 0 | 0 | 80 |
| | 24.00 | 0 | 400 | 0 | 80 | 0 |
| 284 | 12.00 | 0 | 200 | 0 | 0 | 0 |
| | 24.00 | 0 | 400 | 0 | 0 | 0 |
| 285 | 12.00 | 0 | 200 | 0 | 40 | 80 |
| | 24.00 | 0 | 400 | 0 | 0 | 0 |
| 286 | 12.00 | 0 | 200 | 0 | 0 | 0 |
| | 24.00 | 0 | 400 | 0 | 0 | 0 |
| 287 | 12.00 | 0 | 200 | 0 | 0 | 80 |
| | 24.00 | 0 | 400 | 0 | 0 | 0 |
| 288 | 12.00 | 0 | 200 | 0 | 0 | 0 |
| | 24.00 | 0 | 400 | 0 | 0 | 0 |
| 289 | 12.00 | 0 | 200 | 0 | 0 | 0 |
| | 24.00 | 0 | 400 | 0 | 0 | 0 |
| 290 | 12.00 | 0 | 200 | 0 | 80 | 80 |
| | 24.00 | 0 | 400 | 0 | 0 | 0 |
| 291 | 12.00 | 0 | 200 | 0 | 0 | 100 |
| | 24.00 | 0 | 400 | 0 | 0 | 0 |
| 292 | 12.00 | 0 | 200 | 0 | 0 | 30 |
| | 24.00 | 0 | 400 | 0 | 0 | 0 |
| 293 | 12.00 | 0 | 200 | 0 | 0 | 0 |
| | 24.00 | 0 | 400 | 0 | 0 | 0 |
| 294 | 12.00 | 0 | 200 | 0 | 0 | 0 |
| | 24.00 | 0 | 400 | 0 | 0 | 0 |
| 295 | 12.00 | 0 | 200 | 0 | 0 | 0 |
| | 24.00 | 0 | 400 | 0 | 0 | 0 |
| 296 | 12.00 | 0 | 200 | 0 | 0 | 0 |
| | 24.00 | 0 | 400 | 0 | 0 | 80 |
| 297 | 12.00 | 0 | 200 | 100 | 100 | 100 |
| | 24.00 | 0 | 400 | 100 | 100 | 100 |
| 298 | 12.00 | 0 | 200 | 0 | 0 | 0 |
| | 24.00 | 0 | 400 | 0 | 0 | 0 |
| 299 | 12.00 | 0 | 200 | 0 | 0 | 0 |
| | 24.00 | 0 | 400 | 0 | 0 | 0 |
| 300 | 12.00 | 0 | 200 | 20 | 0 | 0 |
| | 24.00 | 0 | 400 | 0 | 0 | 0 |
| 301 | 12.00 | 0 | 200 | 40 | 0 | 0 |
| | 24.00 | 0 | 400 | 0 | 0 | 0 |
| 302 | 12.00 | 0 | 200 | 100 | 100 | 100 |
| | 24.00 | 0 | 400 | 0 | 0 | 100 |
| 303 | 12.00 | 0 | 200 | 0 | 100 | 100 |
| | 24.00 | 0 | 400 | 0 | 0 | 100 |
| 304 | 12.00 | 0 | 200 | 0 | 100 | 100 |
| | 24.00 | 0 | 400 | 0 | 100 | 80 |
| 305 | 12.00 | 0 | 200 | 0 | 0 | 0 |
| | 24.00 | 0 | 400 | 0 | 0 | 0 |

TABLE 17-continued

| COMPOUND EX. NO. | CRW RATE PPM | CRW RESULTS % | SAW SM & MA RATE PPM | SAW RESULTS % | SM RESULTS % | MA RESULTS % |
|---|---|---|---|---|---|---|
| 306 | 12.00 | 0 | 200 | 0 | 100 | 100 |
| | 24.00 | 100 | 400 | 100 | 0 | 0 |
| 307 | 12.00 | 0 | 200 | 0 | 0 | 0 |
| | 24.00 | 0 | 400 | 0 | 0 | 0 |
| 308 | 12.00 | 0 | 200 | 0 | 0 | 80 |
| | 24.00 | 0 | 400 | 0 | 0 | 80 |
| 309 | 12.00 | 0 | 200 | 0 | 40 | 60 |
| | 24.00 | 0 | 400 | 100 | 0 | 0 |
| 310 | 12.00 | 0 | 200 | 0 | 0 | 0 |
| | 24.00 | 0 | 400 | 0 | 0 | 90 |
| 311 | 12.00 | 0 | 200 | 0 | 0 | 0 |
| | 24.00 | 0 | 400 | 0 | 0 | 40 |
| 312 | 12.00 | 0 | 200 | 0 | 0 | 0 |
| | 24.00 | 0 | 400 | 0 | 0 | 0 |
| 313 | 12.00 | | 200 | | | |
| | 24.00 | 0 | 400 | 0 | 30 | 0 |
| 314 | 24.00 | 100 | 400 | 0 | 100 | 100 |
| 317 | 12.00 | 0 | 200 | 80 | 80 | 80 |
| | 24.00 | 0 | 400 | 0 | 0 | 60 |
| 318 | 12.00 | | 200 | | | |
| | 24.00 | 0 | 400 | 0 | 0 | 0 |
| 319 | 12.00 | | 200 | | | |
| | 24.00 | 0 | 400 | 0 | 100 | 100 |
| 320 | 12.00 | 0 | 200 | 0 | 0 | 0 |
| | 24.00 | 0 | 400 | 0 | 0 | 0 |
| 321 | 12.00 | 0 | 200 | 0 | 0 | 0 |
| | 24.00 | 0 | 400 | 0 | 0 | 0 |
| 322 | 12.00 | 0 | 200 | 60 | 100 | 80 |
| | 24.00 | 0 | 400 | 60 | 80 | 100 |
| 323 | 12.00 | 0 | 200 | 0 | 0 | 0 |
| | 24.00 | 0 | 400 | 0 | 0 | 0 |
| 324 | 12.00 | 0 | 200 | 0 | 0 | 0 |
| | 24.00 | 0 | 400 | 0 | 0 | 0 |
| 325 | 12.00 | 0 | 200 | 0 | 0 | 80 |
| | 24.00 | 0 | 400 | 80 | 0 | 0 |
| 326 | 12.00 | 0 | 200 | 0 | 0 | 0 |
| | 24.00 | 0 | 400 | 0 | 0 | 0 |
| 327 | 12.00 | 0 | 200 | 80 | 0 | 100 |
| | 24.00 | 60 | 400 | 0 | 80 | 60 |
| 328 | 12.00 | 100 | 200 | 100 | 80 | 80 |
| | 24.00 | 100 | 400 | 100 | 0 | 0 |

Field Trials

4-[2-[4-(t-Butyl)phenyl]ethoxy]-8-fluoroquinoline (Example 221) was evaluated in a number of field trials. The following table reports the host plants on which it was tested and the pest species against which it showed activity.

TABLE 18

| HOST | PEST |
|---|---|
| alfalfa (Lucerne) | pea aphid, potato leaf hopper, tarnished plant bug, green cloverworm |
| apples | mites, apple aphid, European red mite, green peach aphid, white apple leafhopper, apple rust mite, rosy apple aphid |
| azaleas | greenhouse thrip |
| bean, faba broad | bean aphid |
| broccoli | twospotted spider mite |
| cotton | cotton aphid |
| grape (European) | grape thrip, grape leafhopper |
| hops | Dawson-hop aphid |
| pea, garden (English) | pea aphid |
| pecan nut | yellow hickory aphid |
| privet | thrip |
| sugar beet | green peach aphid |
| wheat | wheat aphid |

Compositions

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or pistontype homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention have been prepared, and are typical of compositions useful in the practice of the present invention.

| A. Aqueous Suspension | |
|---|---|
| 8-Fluoro-N-[2-(2-naphthyl)ethyl]-4-quinolinamine | 12.5% |
| "TERGITOL TMN-6" (nonionic surfactant) | 1.0% |
| "ZEOSYL 200" (silica) | 1.0% |
| "AF-100" (silicon based antifoam agent) | 0.2% |
| 2% xanthan solution | 10.0% |
| "MAKON 10" (10 moles ethyleneoxide nonylphenol surfactant) | 9.0% |
| tap water | 66.3% |

| B. Emulsifiable Concentrate | |
|---|---|
| 4[-2-[4-(t-Butyl)phenyl]ethoxy]-8-fluoroquinoline | 12.4% |
| "EXXON 200" (naphthalene solvent) | 83.6% |
| "TOXIMUL H" (nonionic/anionic surfactant blend) | 2.0% |
| "TOXIMUL D" (nonionic/anionic surfactant blend) | 2.0% |

We claim:

1. A fungicidal method which comprises applying to the locus of a plant pathogen a fungicidally effective but non-pytotoxic amount of a compound of the formula (1)

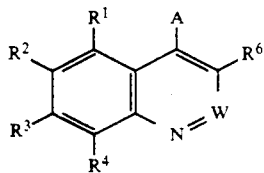

(1)

wherein:

R¹ to R⁴ are independently

H, halo, (C₁-C₄) alkyl, branched (C₃-C₄) alkyl, halo (C₁-C₄) alkyl, (C₁-C₄) alkoxy, NO₂, or NH₂, at least two of R¹ to R⁴ being H, or one of R² to R⁴ is —NR⁷—Y—Ar or O—Y—AR and the rest of R¹ to R⁴ are H;

W is N, or CR⁵;

R⁵ is H, CH₃, Cl, O—Y—Ar, or —NR⁷—Y—Ar;

R⁶ is H, CH₃, Cl, or Br;

A is —O—Alk or —X—Y—Ar;

Alk is a C₂-C₁₈ saturated or unsaturated hydrocarbon chain, straight chain or branched, optionally substituted with halo, halo (C₁-C₄) alkoxy, (C₃-C₈) cycloalkyl, hydroxy, or acetyl;

X is O, NR⁷, or CR⁸R⁹, provided that if one of R² to R⁵ is NR⁷—Y—AR or O—Y—Ar, then X—Y—Ar is an identical group;

R⁷ is H, (C₁-C₄) alkyl, or acetyl;

R⁸ and R⁹ are independently H, (C₁-C₄) alkyl, halo, or OH, or R⁸ and R⁹ combine to form a saturated or unsaturated carbocyclic ring comprising three to seven carbon atoms;

Y is an alkylene chain 2 to 8 carbon atoms long that optionally includes an O, S, SO, SO₂, or NR⁷ group, and optionally includes a saturated or unsaturated carbocyclic ring comprising three to seven carbon atoms, and optionally is substituted with (C₁-C₃) alkyl, (C₂-C₄) alkenyl, phenyl, (C₃-C₈) cycloalkyl, hydroxy, halo, or acety; and Ar is 1,3-benzodioxolyl fluorenyl, pyridyl, substituted pyridyl, indolyl, furanyl, substituted furanyl, thienyl, optionally substituted with CH₃ or Cl, thiazolyl, cyclopentyl, 1-methylcyclopentyl, cyclohexenyl (tetrahydrophenyl), cyclohexyl (hexahydrophenyl), naphthyl, substituted naphthyl, dihydronaphthyl, tetrahydronaphthyl, decahydronaphthyl, or a group of formula (2);

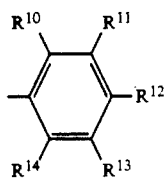

(2)

where

R¹⁰ to R¹⁴ are independently H, halo, (C₁-C₁₀) alkyl, branched (C₃-C₆) alkyl, halo (C₁-C₇) alkyl, (C₁-C₇) alkoxy, halo (C₁-C₇) alkoxy, phenoxy, substituted phenoxy, phenylthio, substituted phenylthio, phenyl, substituted phenyl, NO₂, NH₂, acetoxy, OH. CN, SiR¹⁵R¹⁶R¹⁷, or OSiR¹⁵R¹⁶R¹⁷, where R¹⁵, R¹⁶, and R¹⁷ are independently (C₁-C₄) alkyl or (C₃-C₄) branched alkyl, phenyl, or substituted pehnyl, provided that unless each of R¹⁰ to R¹⁴ is F, CH₃, or H, then at least two of R¹⁰ to R¹⁴ are H:

or an acid addition salt of a compound of formula (1) or an N-oxide of a compound of formula (1) when W is CR⁵;

where, in the foregoing definitions, the term substituted phenyl refers to phenyl substituted with up to three groups selected from halo, (C₁-C₁₀) alkyl, branched (C₃-C₆) alkyl, halo (C₁-C₇) alkyl, hydroxy (C₁-C₇) alkyl, (C₁-C₇) alkoxy, halo (C₁-C₇) alkoxy, phenoxy, phenyl, NO₂, OH, CN, (C₁-C₄) alkanoyloxy, or benzyloxy;

the term substituted phenoxy refers to a phenoxy group substituted with up to three groups selected from halo, (C₁∝C₁₀) alkyl, branched (C₃-C₆) alkyl, halo (C₁-C₇) alkyl, hydroxy (C₁-C₇)alkyl, (C₁-C₇) alkoxy, halo (C₁-C₇) alkoxy, phenoxy, phenyl, NO₂, OH, CN (C₁-C₄) alkanoyloxy, or benzyloxy;

the term substituted phenylthio refers to a phenylthio group substituted with up to three groups selected from halo, (C₁-C₁₀) alkyl, branched (C₃-C₆) alkyl, halo (C₁-C₇) alkoxy, phenoxy, phenyl, NO₂. OH, CN (C₁-C₄) alkanoyloxy, or benzyloxy;

the term substituted phenylsulfonyl refers to a phenylsulfonyl group substituted with up to three groups selected from halo, (C₁-C₁₀) alkyl, branched (C₃-C₆) alkyl, halo (C₁-C₇) alkyl, hydroxy (C₁-C₇) alkyl, (C₁-C₇) alkoxy, halo (C₁-C₇) alkoxy, phenoxy, phenyl, NO₂, OH, CN (C₁-C₄) alkanoyloxy. or benzyloxy; and the terms substituted naphthyl, substituted pyridyl, and substituted furanyl refer to these ring systems substituted with halo, halo (C₁-C₄) alkyl, CN, NO₂, (C₁-C₄) alkyl, (C₃-C₄) branched alkyl, phenyl, (C₁-C₄) alkoxy, or halo (C₁-C₄) alkoxy.

2. A method of claim 1 wherein the compound of formula (1) is one wherein

A is —X—Y—Ar;

R⁸ and R⁹ are independently H or (C₁-C₄) alkyl, or R⁸ and R⁹ combine to form a saturated or unsaturated carbocyclic ring comprising three to seven carbon atoms;

Y is an alkylene chain 2 to 6 carbon atoms long, optionally including a saturated or unsaturated carbocyclic ring comprising three to seven carbon atoms, or substituted with (C₁-C₃) alkyl, phenyl, (C₃-C₈) cycloalkyl, hydroxy, halo, or acetyl; and Ar is 1,3-benzodioxolyl fluorenyl, pyridyl, indolyl, thienyl, optionally substituted with CH₃ or Cl, thiazolyl, cyclohexenyl (tetrahydrophenyl), cyclohexyl (hexahydrophenyl), naphthyl, dihydronaphthyl,
tetrahydronaphthyl,
decahydronaphthyl, or
a group of formula (2);

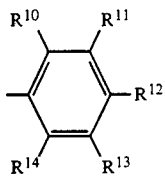

$R^{10}$ to $R^{14}$ are independently H, halo, $(C_1-C_{10})$ alkyl, branched $(C_3-C_6)$ alkyl, halo $(C_1-C_7)$ alkyl, $(C_1-C_7)$ alkoxy, halo $(C_1-C_7)$ alkoxy, phenoxy, substituted phenoxy, phenylthio, substituted phenylthio, phenyl, substituted pehnyl, $NO_2$, OH, or CN, provided that unless each of $R^{10}$ to $R^{14}$ is F, $CH_3$, or H, then at least two of $R^{10}$ to $R^{14}$ are H.

3. A method of claim 1 wherein the compound of formula (1) is one wherein W is CH.

4. A method of claim 1 wherein the compound of formula (1) is one wherein $R^6$ is H.

5. A method of claim 1 wherein the compound of formula (1) is one wherein at least three of $R^1$ to $R^4$ are H.

6. A method of claim 1 wherein the compound of formula (1) is one wherein $R^3$ is Cl or F.

7. A method of claim 1 wherein the compound of formula (1) is one wherein $R^4$ is F.

8. A method of claim 1 wherein the compound of formula (1) is one wherein A is X—Y—Ar.

9. A method of claim 1 wherein the compound of formula (1) is one wherein A is —O—$(CH_2)_2$—Ar.

10. A method of claim 1 wherein the compound of formula (1) is one wherein A is —$NR^7$—$(CH_2)_2$—Ar.

11. A method of claim 1 wherein the compound of formula (1) is one wherein A is —$CR^8R^9$—$(CH_2)_2$—Ar.

12. A method of claim 1 wherein the compound of formula (1) is one wherein Ar is naphthyl.

13. A method of claim 1 wherein the compound of formula (1) is one wherein Ar is thienyl.

14. A method of claim 1 wherein the compound of formula (1) is one wherein Ar is thiazolyl.

15. A method of claim 1 wherein the compound of formula (1) is one wherein Ar is cyclohexenyl.

16. A method of claim 1 wherein the compound of formula (1) is one wherein Ar is an optionally substituted phenyl group of formula (2).

17. A method of claim 1 wherein the compound of formula (1) is one wherein
W is CH;
A is X—$(CH_2)_2$—Ar; and
Ar a group of formula (2)

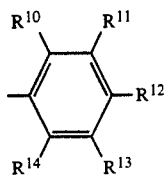

wherein four of $R^{10}$ to $R^{14}$ are H and one of $R^{10}$ to $R^{14}$ is Cl, $(C_1-C_4)$ alkyl, halo $(C_1-C_7)$ alkyl, branched $(C_3-C_6)$ alkyl, $(C_1-C_7)$ alkoxy, halo $(C_1-C_7)$ alkoxy, phenyl, substituted phenyl, phenoxy, or substituted phenoxy.

18. A method of claim 1 wherein the compound of formula (1) is one wherein $R^4$ is F.

19. A fungicidal method of claim 1 wherein the compound of formula (1) is one wherein:
W is CH; 'A is X—Y—Ar;
X is O;
Y is an alkylene chain 2 to 8 carbon atoms long;
Ar is a phenyl group of formula (2) wherein $R^{10}$ to $R^{14}$ are H, halo, I, $(C_1-C_{10})$ alkyl, branched $(C_3-C_6)$ alkyl, halo $(C_1-C_7)$ alkyl, $(C_1-C_7)$ alkoxy, halo $(C_1-C_7)$ alkoxy.

20. A method of claim 17 wherein the compound of Formula (1) is one wherein X is O.

21. A method of claim 20 wherein the compound of Formula (1) is one wherein $R^4$ is F.

22. A method of claim 17 wherein the compound of Formula (1) is one wherein X is NH.

23. A method of claim 17 wherein $R^4$ is F.

24. A method of claim 17 wherein the compound of Formula (1) is one wherein X is $CH_2$.

25. A method of claim 24 wherein $R^4$ is F.

26. A method of claim 21 wherein the compound is selected from:
8-fluoro-4-(2-(3-trifluoromethyl)phenyl)ethoxy)quinoline;
8-fluoro-4-(2-(4-methylphenyl)ethoxy)quinoline;
4-(20(4-(t-butyl)phenyl)ethoxy-8-fluoroquinoline;
8-fluoro-4-(2-(3-(trifluoromethyl)phenyl)ethoxy)quinoline;
8-fluoro-4-(2-(4-methylphenyl)ethoxy)quinoline;
8-fluoro-4(2-(2-(trifluoromethyl)phenyl)ethoxy)quinoline;
4-(2-(4-chlorophenyl)ethoxy)-8-fluoroquinoline;
8-fluoro-4-(2-(2-(trifluoromethyl)phenyl)ethoxy)quinoline;
4-(2-(4-chlorophenyl)ethoxy)-8-fluoroquinoline;
4-(2-(4-methylphenyl)ethoxy)quinoline;
8-fluoro-4-(2-phenylethoxy)quinoline;
8-fluoro-4-(2-phenylethoxy)quinoline;
8-fluoro-4-(2-(3-methylphenyl)ethoxy)quinoline;
8-fluoro-4-(2-(2-fluorophenyl)ethoxy)quinoline;
8-fluoro-4-(2-(2-methoxyphenyl)ethoxy)quinoline; and
8-fluoro-4-(2-(2-methoxyphenyl)ethoxy)quinoline; and
8-fluoro-N-(2-(1,1'-biphenyl)-4-yl-ethoxy)quinoline;
4-(2-(3-chlorophenyl)ethoxy)-8-fluoroquinoline;
8-fluoro-4-(2-(4-(i-propyl)phenyl)ethoxy)quinoline;
8-fluoro-4(2-(3-(trifluoromethyl)phenylethoxy)quinoline;
8-fluoro-4-(2-(4-methoxyphenyl)ethoxy)quinoline;
8-fluoro-4-(2-(3-phenoxyphenyl)ethoxy)quinoline;
8-fluoro-4-(2-(1,1'-biphenyl)-2-yl-ethoxy)quinoline.

27. A method of claim 23 wherein the compound is selected from:
8-fluoro-N-(2-phenylethyl)-4-quinolinamine;
8-fluoro-N-(2-(2-(trifluoromethyl)phenyl)ethyl)-4-quinolinamine;
8-fluoro-N-(2-(3-(trifluoromethyl)phenyl)ethyl)-4-quinolinamine;
N-(2-(4(b   1-methylethyl)phenyl)ethyl)-8-fluoro-4-quinolinamine;
4-(2-(3-chlorophenyl)ethoxy)-8-fluoroquinoline;
N-(2-(4-(i-propyl)-phenyl)ethyl)-8-fluoro-4-quinolinamine;
8-fluoro-N-(2-(3-phenoxyphenyl)ethyl(-4-quinolinamine;

N-(2-(4-(i-propyl)phenyl)ethyl)-8-fluoro-4-quinolinamine;

N-(2-(1,1'-bi-henyl)-3-ylethyl)-8-fluoro-4quinolinamine;

N-(2-(2,4-dichlorophenyl)ethyl)-8-fluoro-4-quinolinamine;

8-fluoro-N-(2-(4-iodophenyl)ethyl)-4-quinoliamine;

N-(2-(4-bromophenyl)ethyl)-8-fluoro-4-quinolinamine;

N-(2-(4-chlorophenyl)ethyl)-8-fluoro-4-quinolinamine;

N-(2-(4-chlorophenyl)ethyl)-N-ethyl-8-fluoro-4-quinolinamine;

N-(3-(1,1'-biphenyl)-4-ylpropyl)-8-fluoro-4-quinolinamine;

8-fluoro-N-(2-(4-phenoxyphenyl)ethyl)-4-quinolinamine;

N-(2-(4-(t-butyl)phenyl)ethyl)-8-fluoro-4-quinolinamine;

N-(2-(4-(i-propyl)phenyl)ethyl)-8-fluoro-4-quinolinamine.

28. A method of claim 25 wherein the compound is selected from:

8-fluoro-4-(3-(4-t-butyl)phenyl)propyl)quinoline;

8-fluoro-4-(3-(4-(i-propyl)phenyl)propyl)quinoline;

8-fluoro-4-(3-phenylpropyl)quinoline;

8-fluoro-4-(3-(4-methylpheny)propyl)quinoline; and 8-fluoro-4-(3-(3-(trifluoromethyl)phenyl)propyl)-quinoline.

* * * * *